United States Patent
Sun et al.

(10) Patent No.: US 10,953,396 B2
(45) Date of Patent: Mar. 23, 2021

(54) METHODS FOR PRODUCING MESOPOROUS ZEOLITE MULTIFUNCTIONAL CATALYSTS FOR UPGRADING PYROLYSIS OIL

(71) Applicant: Saudi Arabian Oil Company, Dhahran (SA)

(72) Inventors: Miao Sun, Dhahran (SA); Ke Zhang, Stoneham, MA (US); Veera Venkata R Tammana, Dhahran (SA)

(73) Assignees: Saudi Arabian Oil Company, Dhahran (SA); Aramco Services Company, Houston, TX (US)

( * ) Notice: Subject to any disclaimer, the term of this patent is extended or adjusted under 35 U.S.C. 154(b) by 0 days.

(21) Appl. No.: 16/502,601

(22) Filed: Jul. 3, 2019

(65) Prior Publication Data

US 2021/0001317 A1    Jan. 7, 2021

(51) Int. Cl.

| | |
|---|---|
| *B01J 29/06* | (2006.01) |
| *B01J 37/02* | (2006.01) |
| *B01J 27/19* | (2006.01) |
| *B01J 27/24* | (2006.01) |
| *B01J 29/04* | (2006.01) |
| *B01J 29/78* | (2006.01) |
| *B01J 35/00* | (2006.01) |
| *B01J 35/10* | (2006.01) |
| *B01J 37/08* | (2006.01) |
| *C10G 35/095* | (2006.01) |
| *B01J 29/70* | (2006.01) |

(52) U.S. Cl.
CPC ........... *B01J 37/0209* (2013.01); *B01J 27/19* (2013.01); *B01J 27/24* (2013.01); *B01J 29/041* (2013.01); *B01J 29/045* (2013.01); *B01J 29/7815* (2013.01); *B01J 35/0006* (2013.01); *B01J 35/109* (2013.01); *B01J 35/1057* (2013.01); *B01J 35/1061* (2013.01); *B01J 37/0201* (2013.01); *B01J 37/0207* (2013.01); *B01J 37/08* (2013.01); *C10G 35/095* (2013.01); *B01J 29/7007* (2013.01); *B01J 2229/186* (2013.01); *B01J 2229/22* (2013.01); *B01J 2229/32* (2013.01); *B01J 2229/38* (2013.01); *C07C 2529/70* (2013.01); *C07C 2529/78* (2013.01); *C10G 2300/1033* (2013.01); *C10G 2300/4006* (2013.01); *C10G 2300/4012* (2013.01); *C10G 2400/30* (2013.01)

(58) Field of Classification Search
CPC .... B01J 29/041; B01J 29/045; B01J 29/7815; B01J 35/0006; B01J 35/1057; B01J 35/1061; B01J 35/109; B01J 37/0201; B01J 37/0207; B01J 2229/186; B01J 2229/22; B01J 2229/32; B01J 2229/38; C07C 2529/70; C07C 2529/78

USPC .......................... 502/60, 73, 85, 86
See application file for complete search history.

(56) References Cited

U.S. PATENT DOCUMENTS

| | | | |
|---|---|---|---|
| 6,531,051 B1 | 3/2003 | Kasztelan et al. | |
| 9,321,973 B2 | 4/2016 | Marchand et al. | |
| 10,118,163 B1 | 11/2018 | Zhang | |
| 2005/0070423 A1 | 3/2005 | Kishan et al. | |
| 2009/0171123 A1* | 7/2009 | Glaser ..................... | B01J 23/44 568/376 |
| 2009/0314683 A1 | 12/2009 | Matsushita | |
| 2013/0143972 A1 | 6/2013 | Townsend et al. | |
| 2013/0164205 A1 | 6/2013 | Putluru et al. | |
| 2013/0178664 A1 | 7/2013 | Zhou et al. | |
| 2013/0245338 A1 | 9/2013 | Weiner et al. | |
| 2014/0021096 A1* | 1/2014 | Chaumonnot ......... | B01J 27/186 208/110 |
| 2014/0027346 A1* | 1/2014 | Chaumonnot ......... | B01J 29/005 208/89 |

(Continued)

FOREIGN PATENT DOCUMENTS

| | | |
|---|---|---|
| CN | 104355995 A | 2/2015 |
| CN | 106622354 A | 5/2017 |

(Continued)

OTHER PUBLICATIONS

Passoni et al., "Heterogenization of H6PMo9V3O40 and palladium actetate in VPI-5 and MCM-41 and their use in the catalytic oxidation of benzene to phenol", Journal of Molecular Catalysis A: Chemical 134 (1998), pp. 229-235.*

Kumar et al., "MCM-41, MCM-48 and related mesoporous adsorbents: their synthesis and characterization", Colloids and Surfaces A: Physicochemical and Engineering Aspects 187-188 (2001), pp. 109-116.*

Technical Data Sheet, ACS Material Al_MCM-41, www.acsmaterial.com, no date available.*

Guerzoni et al. "Catalytic Cracking of a Hydrocarbon Mixture on Combinations of HY and HZSM-5 Zeolites" Chemistry Department, Journal of Catalysis 139, 289-303 (1993), 15 pgs.

(Continued)

*Primary Examiner* — Elizabeth D Wood
(74) *Attorney, Agent, or Firm* — Dinsmore & Shohl LLP

(57) ABSTRACT

A method of making a multifunctional catalyst for upgrading pyrolysis oil includes contacting a hierarchical mesoporous zeolite support with a solution including at least a first metal catalyst precursor and a second metal catalyst precursor, each or both of which may include a heteropolyacid. The hierarchical mesoporous zeolite support may have an average pore size of from 2 nm to 40 nm. Contacting the hierarchical mesoporous zeolite support with the solution deposits or adsorbs the first metal catalyst precursor and the second catalyst precursor onto outer surfaces and pore surfaces of the hierarchical mesoporous zeolite support to produce a multifunctional catalyst precursor. The method further includes removing excess solution and calcining the multifunctional catalyst precursor to produce the multifunctional catalyst comprising at least a first metal catalyst and a second metal catalyst deposited on the outer surfaces and pore surfaces of the hierarchical mesoporous zeolite support.

17 Claims, 2 Drawing Sheets

(56) References Cited

U.S. PATENT DOCUMENTS

| | | | |
|---|---|---|---|
| 2015/0231615 | A1 | 8/2015 | Bonduelle et al. |
| 2015/0274620 | A1 | 10/2015 | Zong et al. |
| 2017/0001180 | A1* | 1/2017 | Ravishankar ............ B01J 29/26 |
| 2017/0100710 | A1 | 4/2017 | Kim et al. |
| 2018/0290131 | A1 | 10/2018 | Carrette |
| 2018/0333708 | A1 | 11/2018 | Ding et al. |
| 2019/0134616 | A1 | 5/2019 | Jae et al. |

FOREIGN PATENT DOCUMENTS

| | | |
|---|---|---|
| FR | 3075663 A1 | 6/2019 |
| WO | 2012085358 A1 | 6/2012 |
| WO | 2017207976 A1 | 12/2017 |

OTHER PUBLICATIONS

Hanif et al. "Supported solid and heteropoly acid catalysts for production of biodiesel" Catalysis Reviews (2017) vol. 59, No. 2, 165-188, 24 pgs.

Jimenez-Cruz et al."Molecular size evaluation of linear and branched paraffins from the gasoline pool by DFT quantum chemical calculations" Science Direct, Fuel 83 (2004) 2183-2188, 7 pgs.

Kim et al. "Novel Ni2P/zeolite catalysts for naphthalene hydrocracking to BTX" Catalysis Communications 45 (2014) 133-138, 6 pgs.

Kim et al. "Morphology effect of b-zeolite supports for Ni2P catalysts on the hydrocracking of polycyclic aromatic hydrocarbons to benzene, toluene, and xylene" Journal of Catalysis 351 (2017) 67-78, 12 pgs.

Lapinas et al. "Catalytic Hydrogenation and Hydrocracking of Fluorene: Reaction Pathways, Kinetics, and Mechanisms" Ind. Eng. Chem. Res. 1991, 30, 42-50, 9 pgs.

Leite et al. "Hydrocracking of phenanthrene over bifunctional Pt catalysts" Catalysis Today 65 (2001) 241-247, 7 pgs.

Lemberton et al. "Catalytic hydroconversion of simulated coal tars" Applied Catalysis A: General, 79 (1991) 115-126, 12 pgs.

Matsui et al. "Explanation of Product Distribution of Hydrocracking Reaction of Aromatic Hydrocarbons with Nickel-Loaded Zeolites Based on CAMD Study on Interaction between Zeolites and Substrates" Energy & Fuels (1995) 9, 435-438, 4 pgs.

Okuhara et al. "Catalytic Chemistry of Heteropoly Compounds" Advances in Catalysis, Adv Cata vol. 41 (1996) 113, 140 pgs.

Park et al. "Hydro-conversion of 1-methyl naphthalene into (alkyl)benzenes over alumina-coated USY zeolite-supported NiMoS catalysts" Fuel 90 (2011) 182-189, 8 pgs.

Park et al. "Mild hydrocracking of 1-methyl naphthalene (1-MN) over alumina modified zeolite" Journal of Industrial and Engineering Chemistry 19 (2013) 627-632, 6 pgs.

Tailleur et al. The effect of aromatics on paraffin mild hydrocracking reactions (WNiPd/CeY—Al2O3), Fuel Processing Technology 89 (2008) 808-818, 11 pgs.

Upare et al. "Cobalt promoted Mo/beta zeolite for selective hydrocracking of tetralin and pyrolysis fuel oil into monocyclic aromatic hydrocarbons" Journal of Industrial and Engineering Chemistry 35 (2016) 99-107, 9 pgs.

Upare et al. "Selective hydrocracking of pyrolysis fuel oil into benzene, toluene and xylene over CoMo/beta zeolite catalyst" Journal of Industrial and Engineering Chemistry 46 (2017) 356-363, 8 pgs.

Office Action dated Jan. 6, 2020 pertaining to U.S. Appl. No. 16/502,633, filed Jul. 3, 2019, 19 pgs.

Wang, et al., "Performance Evaluation of "Ship-In-The-Bottle" Type Heteropoly Acid Encaged Y-Type Zeolite As Catalyst for Oxidative Desulfurization", collect. czech. commun. 2011, vol. 76, No. 12, pp. 1595-1605.

International Search Report and Written Opinion dated Apr. 14, 2020 pertaining to International application No. PCT/US2019/068539 filed Dec. 26, 2019.

International Search Report and Written Opinion dated May 27, 2020 pertaining to International application No. PCT/US2020/019620 filed Feb. 25, 2020, 15 pgs.

U.S. Notice of Allowance and Fee(s) due dated Aug. 19, 2020 pertaining to U.S. Appl. No. 16/807,451, filed Mar. 3, 2020, 20 pgs.

Notice of Allowance and Fee(s) Due dated Jul. 16, 2020 pertaining to U.S. Appl. No. 16/807,971, filed Mar. 3, 2020, 16 pgs.

Office Action dated Nov. 9, 2020 pertaining to U.S. Appl. No. 16/916,234, filed Jun. 30, 2020, 30 pgs.

Office Action dated Nov. 9, 2020 pertaining to U.S. Appl. No. 16/502,633, filed Jul. 3, 2020, 16 pgs.

Nikulshin et al. "CoMo/Al2O3 catalysts prepared on the basis of Co2Mo10-heteropolyacid and cobalt citrate: Effect of Co/Mo ratio", Fuel, vol. 100, Oct. 2012, pp. 24-33.

Office Action dated Nov. 19, 2020 pertaining to U.S. Appl. No. 16/909,114, filed Jun. 23, 2020, 24 pgs.

* cited by examiner

METHODS FOR PRODUCING MESOPOROUS ZEOLITE MULTIFUNCTIONAL CATALYSTS FOR UPGRADING PYROLYSIS OIL

TECHNICAL FIELD

The present specification generally relates to multifunctional catalysts and methods for producing the multifunctional catalysts for upgrading pyrolysis oil.

BACKGROUND

Crude oil can be converted to valuable chemical intermediates and products through one or more hydrotreating processes. The hydrotreating processes can include steam cracking, in which larger hydrocarbons in the crude oil are cracked to form smaller hydrocarbons. Steam cracking units produce a bottom stream, which is referred to as pyrolysis oil. The pyrolysis oil may include an increased concentration of aromatic compounds compared to the crude oil feedstock. In many crude oil processing facilities, this pyrolysis oil is burned as fuel. However, the aromatic compounds in the pyrolysis oil can be converted to valuable chemical intermediates and building blocks. For example, aromatic compounds from the pyrolysis oil can be converted into xylenes, which can be initial building blocks for producing terephthalic acid, which can then be used to produce polyesters. The aromatic compounds in the pyrolysis oil can be used to produce many other valuable aromatic intermediates. The market demand for these valuable aromatic intermediates continues to grow.

SUMMARY

Accordingly, ongoing needs exist for improved multifunctional catalysts for upgrading pyrolysis oils. Pyrolysis oils from steam cracking processes can be upgraded to produce valuable aromatic intermediates by contacting the pyrolysis oil with catalysts operable to convert multi-ring aromatic compounds in the pyrolysis oil to one or more C6-C8 aromatic compounds, which can include benzene, toluene, ethylbenzene, xylenes, other aromatic compounds, or combinations of these. Existing catalysts operable to upgrade pyrolysis oil can include multi-metal hydrocracking catalysts that have 2 or more metals supported on a catalyst support. These multi-metal hydrocracking catalysts are typically prepared from conventional metal precursors, such as metallate hydrates, metal nitrates, and other conventional metal precursors impregnated onto the microporous catalyst supports.

With these multi-metal hydrocracking catalysts prepared from conventional metal precursors, large aromatic compounds (greater than 8 carbon atoms) can be converted to C6-C8 aromatic compounds at reaction temperatures in a range of 380 degrees Celsius (° C.) to 400° C. and pressures of from 6 megapascals (MPa) to 8 MPa. Maintaining the pressure in a range of 6 MPa to 8 MPa may require a greater pressure resistance of the facility and may consume a greater amount of energy compared to lesser pressure systems. In other words, the use of existing multi-metal hydrocracking catalysts to upgrade pyrolysis oil requires expensive equipment rated for greater operating pressures and can consume greater amounts of energy to maintain the pressure above 6 MPa. Reducing the pressure below 6 MPa can substantially reduce the yield of C6-C8 aromatics when upgrading using these existing multi-metal hydrocracking catalysts prepared from conventional metal catalyst precursors.

Additionally, these conventional multi-metal hydrocracking catalysts may be prepared using zeolite supports, which may generally be microporous having an average pore size of less than about 2 nanometers (nm). However, the multi-ring aromatic compounds present in pyrolysis oil may have molecular sizes that are larger than the average pore size of zeolite supports used to prepare these conventional multi-metal catalysts. Thus, the small average pore size of the nanoporous zeolites may restrict access of the larger multi-ring aromatic compounds to reactive sites within the pores of the zeolite support, thus, reducing the yield and conversion attainable with these existing multi-metal hydrocracking catalysts.

The present disclosure is directed to multifunctional catalysts for upgrading pyrolysis oil. The multifunctional catalysts of the present disclosure are prepared from a hierarchical mesoporous zeolite support, and a heteropolyacid may be used for at least one of the metal precursors. The present disclosure is also directed to methods of making the multifunctional catalyst and methods of upgrading pyrolysis oil using the multifunctional catalyst. The multifunctional catalyst of the present disclosure may produce greater yields of C6-C8 aromatic compounds from upgrading pyrolysis oil at reduced reaction pressures compared to upgrading pyrolysis oil using existing multi-metal hydrocracking catalysts. The multifunctional catalyst of the present disclosure can be prepared by contacting a hierarchical mesoporous zeolite support with a solution containing a first metal catalyst precursor and a second metal catalyst precursor, where at least one of the first or second metal catalyst precursor is a heteropolyacid. The hierarchical mesoporous zeolite support may have an average pore size of from 2 nm to 40 nm. The heteropolyacid is a compound that may include at least an acidic hydrogen, a transition metal, at least one heteroatom, and oxygen. It has been discovered that preparing the multifunctional catalyst using a heteropolyacid for at least one of the metal precursors in place of a conventional metal precursor produces a multifunctional catalyst that achieves a greater yield of C6-C8 aromatic compounds at reduced reaction pressures compared to the multi-metal hydrocracking catalysts that are currently used to upgrade pyrolysis oil. It has also been discovered that preparing the multifunctional catalyst from a hierarchical mesoporous zeolite support may further increase the yield of C6-C8 aromatic compounds at reduced reaction pressures. The improved yield and reduced operating pressure may increase the efficiency of upgrading pyrolysis oil and may reduce the capital and operating costs of the process for upgrading pyrolysis oil.

According to one or more aspects of the present disclosure, a method for producing a multifunctional catalyst for upgrading pyrolysis oil may include contacting a hierarchical mesoporous zeolite support with a solution comprising at least a first metal catalyst precursor and a second metal catalyst precursor. The hierarchical mesoporous zeolite support may have an average pore size of from 2 nanometers to 40 nanometers as determined by Barrett-Joyner-Halenda (BJH) analysis. The first metal catalyst precursor, the second metal catalyst precursor, or both, may include a heteropolyacid. The contacting may deposit the first metal catalyst precursor and the second catalyst precursor onto outer surfaces and pore surfaces of the hierarchical mesoporous zeolite support to produce a multifunctional catalyst precursor. The method may further include removing excess solution from the multifunctional catalyst precursor and calcining the multifunctional catalyst precursor to produce the multifunctional catalyst comprising at least a first metal catalyst and a second metal catalyst deposited on the outer surfaces and pore surfaces of the hierarchical mesoporous zeolite support.

According to one or more other aspects of the present disclosure, a multi-functional catalyst for upgrading pyrolysis oil may be produced by a process that includes contacting a hierarchical mesoporous zeolite support with a solution comprising at least a first metal catalyst precursor and a second metal catalyst precursor. The hierarchical mesoporous zeolite support may have an average pore size of from 2 nanometers to 40 nanometers as determined by B arrett-Joyner-Halenda (BJH) analysis, the first metal catalyst precursor, the second metal catalyst precursor, or both, may comprise a heteropolyacid, and the contacting may deposit the first metal catalyst precursor and the second catalyst precursor onto outer surfaces and pore surfaces of the hierarchical mesoporous zeolite support to produce a multifunctional catalyst precursor. The process may further include removing excess solution from the multifunctional catalyst precursor and calcining the multifunctional catalyst precursor to produce the multifunctional catalyst. The multifunctional catalyst may include at least a first metal catalyst and a second metal catalyst deposited on the outer surfaces and the pore surfaces of the zeolite support.

According to one or more other aspects of the present disclosure, a multi-functional catalyst for upgrading pyrolysis oil may include one or more cobalt compounds, one or more molybdenum compounds, and phosphorous supported on a hierarchical mesoporous zeolite support. At least one of the molybdenum compounds, cobalt compounds, or phosphorous may be provided by a heteropolyacid precursor, and the hierarchical mesoporous zeolite support may have an average pore size of from 2 nanometers to 40 nanometers as determined by BJH analysis.

According to still other aspects of the present disclosure, a method for upgrading pyrolysis oil may include contacting the pyrolysis oil with a multifunctional catalyst at mild reaction conditions comprising reaction temperatures of less than 500 degrees Celsius (° C.) and pressures less than 6 megapascals (MPa). The pyrolysis oil may include multi-ring aromatic compounds. The multifunctional catalyst may be produced by a process comprising contacting a hierarchical mesoporous zeolite support with a solution comprising at least a first metal catalyst precursor and a second metal catalyst precursor. The hierarchical mesoporous zeolite support may have an average pore size of from 2 nanometers to 40 nanometers as determined by Barrett-Joyner-Halenda (BJH) analysis, the first metal catalyst precursor, the second metal catalyst precursor, or both, may include a heteropolyacid, and the contacting may deposit the first metal catalyst precursor and the second catalyst precursor onto outer surfaces and pore surfaces of the hierarchical mesoporous zeolite support to produce a multifunctional catalyst precursor. The process for producing the multifunctional catalyst may further include removing excess solution from the multifunctional catalyst precursor and calcining the multifunctional catalyst precursor to produce the multifunctional catalyst. The multifunctional catalyst comprises at least a first metal catalyst and a second metal catalyst supported on the zeolite support. Contact of the pyrolysis oil with the multifunctional catalyst at the reaction conditions may convert at least a portion of the multi-ring aromatic compounds in the pyrolysis oil to one or more C6-C8 aromatic compounds.

Additional features and advantages of the described embodiments will be set forth in the detailed description, which follows, and in part will be readily apparent to those skilled in the art from that description or recognized by practicing the described embodiments, including the detailed description, which follows, the claims, as well as the appended drawings.

BRIEF DESCRIPTION OF THE DRAWINGS

The following detailed description of specific embodiments of the present disclosure can be best understood when read in conjunction with the following drawings, in which like structure is indicated with like reference numerals and in which.

Figure 1:
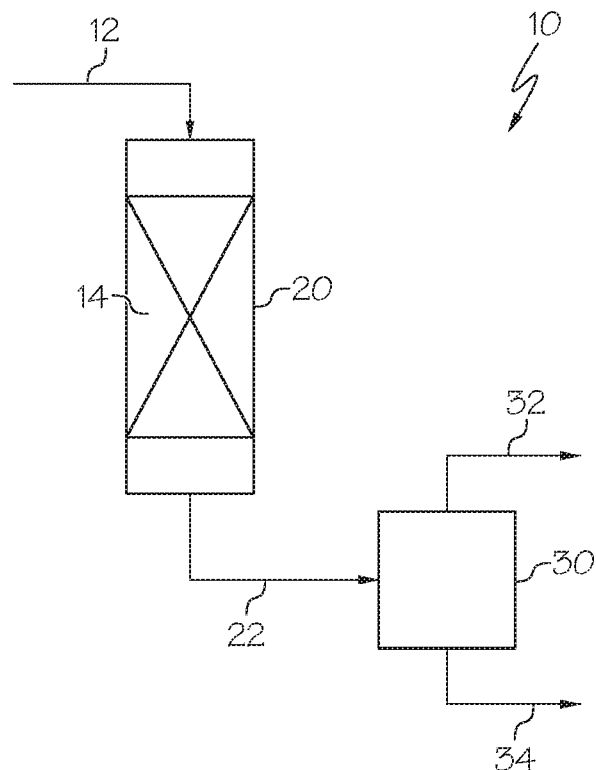
FIG. 1 schematically depicts a reactor system for upgrading pyrolysis oil, according to one or more embodiments described in this disclosure.
Figure 3:
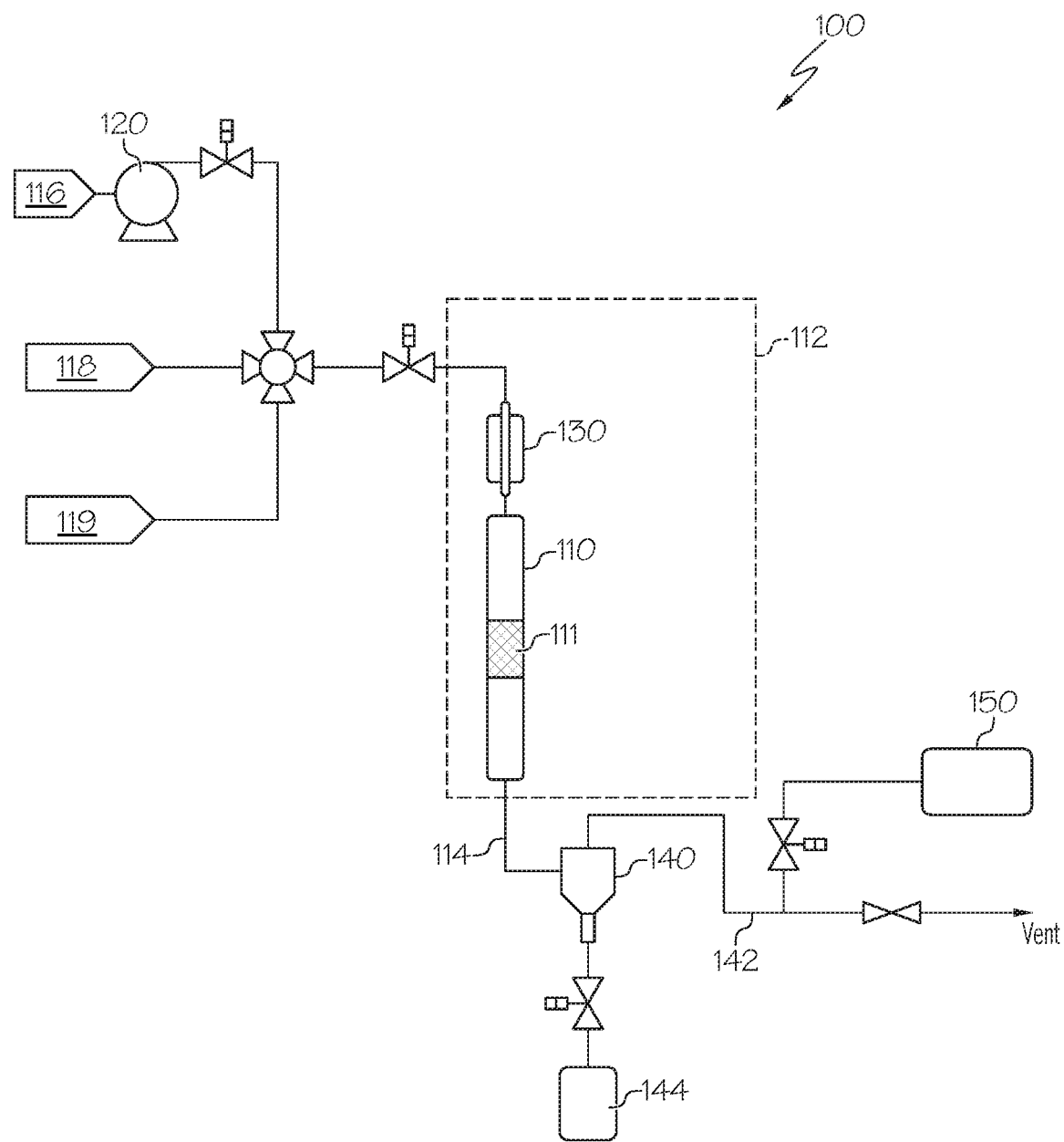
FIG. 3 schematically depicts a reactor system for upgrading a model pyrolysis oil in the Examples, according to one or more embodiments described in this disclosure.

For the purposes of describing the simplified schematic illustrations and descriptions of FIGS. 1 and 3, the numerous valves, temperature sensors, flow meters, pressure regulators, electronic controllers, pumps, and the like that may be employed and well known to those of ordinary skill in the art of certain chemical processing operations are not included. Further, accompanying components that are often included in typical chemical processing operations, such as valves, pipes, pumps, agitators, heat exchangers, instrumentation, internal vessel structures, or other subsystems may not be depicted. Though not depicted, it should be understood that these components are within the spirit and scope of the present embodiments disclosed. However, operational components, such as those described in the present disclosure, may be added to the embodiments described in this disclosure.

Arrows in the drawings refer to process streams. However, the arrows may equivalently refer to transfer lines, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows that do not connect two or more system components may signify a product stream which exits the depicted system or a system inlet stream which enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1 and 3. Mixing or combining may also include mixing by directly introducing both streams into a like system component, such as a separation unit, reactor, or other system component. For example, it should be understood that when two streams are depicted as being combined directly prior to entering a system component, the streams could equivalently be introduced into the system component separately and be mixed in the system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to multifunctional catalysts for upgrading pyrolysis oil. The multifunctional catalysts may include a plurality of metal catalysts supported on a hierarchical mesoporous zeolite support. The hierarchical mesoporous zeolite support may have an average pore size of from 2 nanometers (nm) to 40 nm, or from 5 nm to 25 nm. In some embodiments, the hierarchical mesoporous zeolite support may be a hierarchical mesoporous beta zeolite support. The multifunctional catalysts of the present disclosure can be prepared using a heteropolyacid for at least one of the metal catalyst precursors. The multifunctional catalysts for upgrading pyrolysis oil of the present disclosure made using heteropolyacids for the metal catalyst precursors and having a hierarchical mesoporous zeolite support may provide greater yield of valuable aromatic compounds, such as benzene, toluene, ethylbenzene, and xylenes, from upgrading of the pyrolysis oil. Additionally, the multifunctional catalysts for upgrading pyrolysis oil may enable the upgrading of pyrolysis oil to be conducted at lesser reaction pressures compared to existing commercially available catalysts for upgrading pyrolysis oil.

As used in this disclosure, the term "C6-C8 aromatic compounds" may refer to one or more compounds having an aromatic ring, with or without substitution, and from 6 to 8 carbon atoms. The term "BTEX" may refer to any combination of benzene, toluene, ethylbenzene, para-xylene, meta-xylene, and ortho-xylene.

As used in this disclosure, the term "xylenes," when used without a designation of the isomer, such as the prefix para, meta, or ortho, may refer to one or more of meta-xylene, ortho-xylene, para-xylene, and mixtures of these xylene isomers.

As used in this disclosure, the terms "upstream" and "downstream" refer to the relative positioning of unit operations with respect to the direction of flow of the process streams. A first unit operation of a system is considered "upstream" of a second unit operation if process streams flowing through the system encounter the first unit operation before encountering the second unit operation. Likewise, a second unit operation is considered "downstream" of the first unit operation if the process streams flowing through the system encounter the first unit operation before encountering the second unit operation.

As used in this disclosure, the term "outer surfaces" may refer to surfaces at the outer periphery of a catalyst or catalyst support, such as the hierarchical mesoporous zeolite support.

As used in this disclosure, the term "pore surfaces" may refer to the inner surfaces of pores in a catalyst or catalyst support, where the pores include at least the pores in fluid communication with the outer surfaces of the catalyst or catalyst support and are accessible to reactants.

As used in this disclosure, the "average pore size" of a catalyst or catalyst support may refer to the average pore size determined by Barrett-Joyner-Halenda (BJH) analysis. BJH analysis measures the amount of a gas (argon) that detaches from a material, such as the hierarchical mesoporous zeolite support, at 87 Kelvin over a range of pressures. Using the Kelvin equation, the amount of argon adsorbate removed from the pores of the material and the relative pressure of the system can be used to calculate the average pore size of the material.

Referring now to FIG. 1, a system 10 for upgrading pyrolysis oil 12 is schematically depicted. The system 10 for upgrading pyrolysis oil 12 may include a reactor unit 20 and a separation unit 30 downstream of the reactor unit 20. The reactor unit 20 may include one or a plurality of reactors and may be operable to contact the pyrolysis oil 12 with a catalyst in reaction zone 14 to produce an upgraded effluent 22. The catalyst may be the multifunctional catalyst of the present disclosure. The upgraded effluent 22 may be passed to the separation unit 30, which may include one or a plurality of separation processes or unit operations. The separation unit 30 may be operable to separate the upgraded effluent 22 into one or a plurality of product streams, such as a BTEX-containing stream and a greater boiling fraction 34. Although the separation unit 30 is depicted in FIG. 1 as separating the upgraded effluent 22 into the C6-C8 aromatic stream 32 and a greater boiling fraction 34, it is understood that the separation unit 30 may be operable to separate the upgraded effluent 22 into a plurality of product streams, one of which may include a C6-C8 aromatic stream 32.

Figure 2:
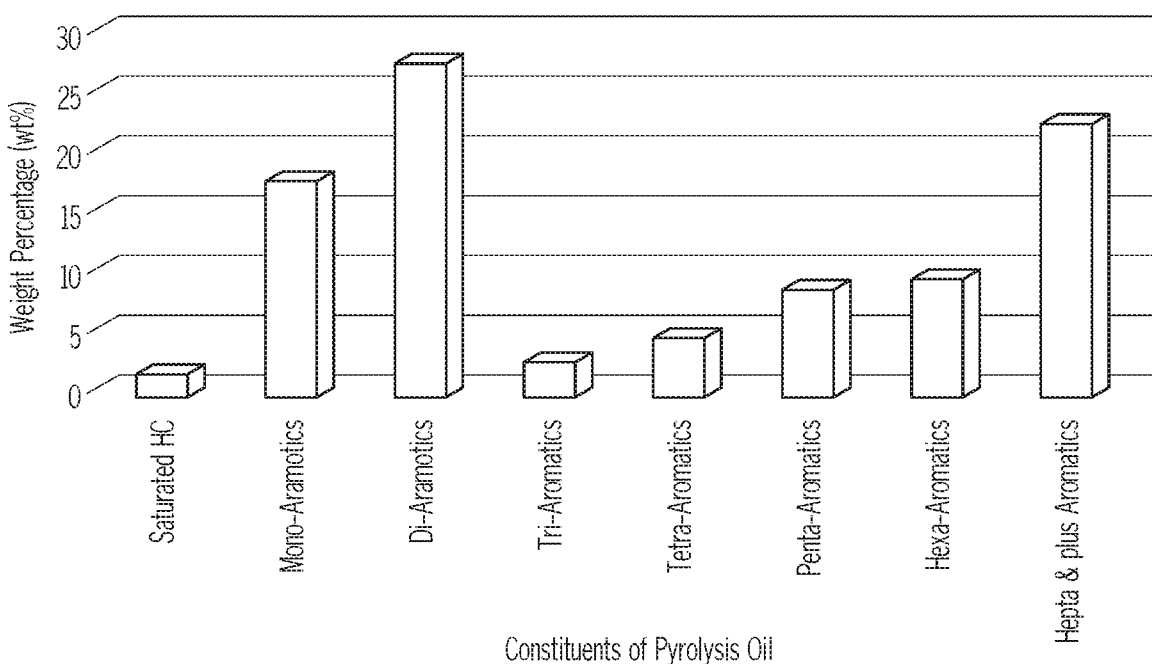
FIG. 2 graphically depicts an example composition for pyrolysis oil obtained from a steam cracking process for steam cracking crude oil, according to one or more embodiments described in this disclosure.

The pyrolysis oil 12 may be a stream from a hydrocarbon processing facility that is rich in aromatic compounds, such as multi-ring aromatic compounds. In some embodiments, the pyrolysis oil may be a bottom stream from a steam cracking process. The pyrolysis oil 12 may include mono-aromatic compounds and multi-aromatic compounds. Multi-aromatic compounds may include aromatic compounds including 2, 3, 4, 5, 6, 7, 8, or more than 8 aromatic ring structures. The pyrolysis oil 12 may also include other components, such as but not limited to saturated hydrocarbons. Referring to FIG. 2, the composition of a typical pyrolysis oil produced from steam cracking crude oil from Saudi Arabia is depicted. As shown in FIG. 2, the pyrolysis oil may include mono-aromatics, di-aromatics, tri-aromatics, tetra-aromatics, penta-aromatics, hexa-aromatics, and aromatic compounds having 7 or more aromatic rings (hepta & plus aromatics in FIG. 2). The pyrolysis oil may include elevated concentrations of di-aromatic compounds and aromatic compounds having greater than or equal to 7 aromatic rings, as indicated by FIG. 2. In some embodiments, the pyrolysis oil that is rich in multi-aromatic compounds may include greater than or equal to 50 weight percent (wt. %) multi-aromatic compounds, such as greater than or equal to 60 wt. %, greater than or equal to 65 wt. %, greater than or equal to 70 wt. %, greater than or equal to 75 wt. %, or even greater than or equal to 80 wt. % multi-aromatic compounds based on the unit weight of the pyrolysis oil. The pyrolysis oil may also have a low concentration of sulfur and sulfur compounds. The pyrolysis oil may have a concentration of sulfur and sulfur-containing compounds of less than or equal to 500 parts per million by weight (ppmw), such as less than or equal to 400 ppmw, or even less than or equal to 300 ppmw.

The multi-aromatic compounds in the pyrolysis oil may be upgraded to C6-C8 aromatic compounds through contact with the catalyst at the reaction temperature and pressure. Converting di-aromatic and multi-aromatic compounds to C6-C8 aromatic compounds, such as benzene, toluene, ethylbenzene, and xylenes, is a complicated reaction that may include multiple synchronized and selective reactions, which may include selective hydrogenation of one aromatic ring in a compound but not all, subsequent ring opening of the saturated naphthenic ring, hydro-dealkylation, and transalkylation. For example, in one embodiment, upgrading pyrolysis oil may include selective hydrogenation of at least one aromatic ring structure or a multi-ring aromatic compound to produce a molecule with one or more aromatic rings and at least one saturated ring. The saturated ring portion may then undergo ring opening to produce a substituted aromatic. The substituted aromatic may then undergo one or more of hydroalkylation, transalkylation, or disproportionation to produce C6-C8 aromatic compounds. It is understood that multiple variations and combinations of these reactions as well as other chemical reactions may occur during the upgrading process.

This complex sequence of synchronized reactions for upgrading pyrolysis oil may be catalyzed using a multimetallic catalyst having at least catalytic transition metals. In conventional upgrading processes, the catalyst used to upgrade the pyrolysis oil may be a multi-metal hydrocracking catalyst. These multi-metal hydrocracking catalysts are often synthesized using conventional metal precursors, such as metallate hydrates, metal nitrates, metal carbonates, metal hydroxides, other conventional metal precursors, or combinations of these conventional metal precursors.

With these multi-metal hydrocracking catalysts made from conventional metal precursors, large aromatic compounds (greater than 8 carbon atoms) can be converted to C6-C8 aromatic compounds, such as but not limited to benzene, toluene, ethylbenzene, or xylenes (BTEX), at reaction temperatures in a range of 380 degrees Celsius (° C.) to 400° C. and pressures of from 6 megapascals (MPa) to 8 MPa. Maintaining the pressure in a range of 6 MPa to 8 MPa may require a greater pressure resistance of the facility and may consume a greater amount of energy compared to reactions conducted on lesser reaction pressures. In other words, the use of existing multi-metal hydrocracking catalysts to upgrade pyrolysis oil may require expensive equipment, which is rated for greater operating pressures, and can consume greater amounts of energy to maintain the pressure above 6 MPa. Additionally, the yield of C6-C8 aromatic compounds using these existing multi-metal hydrocracking catalysts is low. Reducing the pressure below 6 MPa can further reduce the yield of C6-C8 aromatic compounds when upgrading using existing multi-metal hydrocracking catalysts.

Additionally, these conventional multi-metal hydrocracking catalysts may be prepared using zeolite supports, which may generally be microporous materials having an average pore size of less than about 2 nm or even less than about 1 nm as determined using the BJH method. However, the multi-ring aromatic compounds present in pyrolysis oil may have molecular sizes that are larger than the average pore size of zeolite supports used to prepare these conventional multi-metal catalysts. For example, a typical beta zeolite support may have an average pore size of about 6.7 angstroms (Å), which is smaller than the molecular size of tri-aromatic compounds (8.171 Å), tetra-aromatic compounds (8.562 Å), and penta-aromatic compounds (8.577 Å). The molecular sizes of the tri-aromatic, tetra-aromatic, and penta-aromatic compounds are provided for the molecules without any substitution on the aromatic rings. The small average pore size of the nanoporous zeolites may restrict access of the larger multi-ring aromatic compounds to reactive sites within the pores of the zeolite support, thus, reducing the yield and conversion that is attainable with these catalysts.

As previously discussed, the present disclosure is directed to a multifunctional catalyst for upgrading pyrolysis oil, the multifunctional catalyst being produced by depositing a plurality of metal catalysts onto at least the outer surfaces and pore surfaces of a hierarchical mesoporous zeolite support, where at least one of the metal catalysts is provided by a heteropolyacid utilized as a metal catalyst precursor. The present disclosure is also directed to the multifunctional catalysts prepared by the disclosed methods and methods of upgrading pyrolysis oil using the disclosed multifunctional catalysts. The methods of the present disclosure for making the multifunctional catalyst for upgrading pyrolysis oil may include contacting the hierarchical mesoporous zeolite support with a solution comprising at least a first metal catalyst precursor and a second metal catalyst precursor. The first metal catalyst precursor, the second metal catalyst precursor, or both, may include a heteropolyacid. The hierarchical mesoporous zeolite support may have an average pore size of from 2 nm to 40 nm, or from 5 nm to 25 nm as determined using the BJH method. Contacting the hierarchical mesoporous zeolite support with the solution may result in deposition or adsorption of the first metal catalyst precursor and the second catalyst precursor onto outer surfaces and pore surfaces of the hierarchical mesoporous zeolite support to produce a multifunctional catalyst precursor. The method may further include removing the excess solution and solvent from the multifunctional catalyst precursor and calcining the multifunctional catalyst precursor to produce the multifunctional catalyst, which includes at least a first metal catalyst and a second metal catalyst deposited on the outer surfaces and pore surfaces of the zeolite support.

The multifunctional catalysts made by the methods of the present disclosure may increase the yield of BTEX from upgrading pyrolysis oil compared to existing multi-metal hydrocracking catalysts. Additionally, as compared to existing multi-metal hydrocracking catalysts, the multifunctional catalysts made by the methods of the present disclosure may also enable the process for upgrading pyrolysis oil to be conducted at the same reaction temperature and reduced reaction pressure, such as a reaction pressure less than or equal to 5 MPa. The reduced reaction pressure enabled by the multifunctional catalysts of the present disclosure may reduce the capital and operating costs of systems for upgrading pyrolysis oils.

The method of making the multi-functional catalysts may include providing a hierarchical mesoporous zeolite support. The hierarchical mesoporous zeolite support may have an average pore size sufficient to enable multi-ring aromatic compounds to access reactive sites within the pores of the hierarchical mesoporous zeolite support. The hierarchical mesoporous zeolite support may have an average pore size of greater than or equal to 2 nm, greater than or equal to 5 nm, or even greater than or equal to 8 nm as determined using the BJH method. The hierarchical mesoporous zeolite support may have an average pore size less than or equal to 40 nm, less than or equal to 30 nm, or even less than or equal to 25 nm as determined using the BJH method. In some embodiments, the hierarchical mesoporous zeolite support may have an average pore size of from 2 nm to 40 nm, from 2 nm to 30 nm, from 2 nm to 25 nm, from 5 nm to 40 nm, from 5 nm to 30 nm, from 5 nm to 25 nm, from 8 nm to 40 nm, from 8 nm to 30 nm, or from 8 nm to 25 nm, where the average pore size is determined using the BJH method.

The hierarchical mesoporous zeolite support may have a molar ratio of silica ($SiO_2$) to alumina ($Al_2O_3$) of greater than or equal to 10, such as greater than or equal to 20, greater than or equal to 30, greater than or equal to 40, greater than or equal to 50, or greater than or equal to 60. The zeolite support may have a molar ratio of of $SiO_2$ to $Al_2O_3$ of less than or equal to 70, such as less than or equal to 60, less than or equal to 50, less than or equal to 40, less than or equal to 30, or even less than or equal to 20. The zeolite support may have a molar ratio of of $SiO_2$ to $Al_2O_3$ of from 10 to 70. In some embodiments, the zeolite support may have a molar ratio of $SiO_2$ to $Al_2O_3$ of from 10 to 60, from 10 to 50, from 10 to 40, from 20 to 70, from 20 to 60, from 20 to 50, from 20 to 40, from 30 to 70, from 30 to 60, from 30 to 50, from 40 to 70, from 40 to 60, from 50 to 70, or from 10 to 30. In some embodiments, the hierarchical mesoporous zeolite support may be a hierarchical mesoporous beta zeolite support. In some embodiments, the hierarchical mesoporous beta zeolite support may have an average pore size of 2 nm to 40 nm, or from 5 nm to 25 nm.

The hierarchical mesoporous zeolite support may be prepared from a parent microporous zeolite through a desilication process, in which silica may be removed from the zeolite to increase the average pore size. A desilication method of preparing the hierarchical mesoporous zeolite support may include providing a microporous parent zeolite with a silica to alumina ($SiO_2/Al_2O_3$) ratio of at least 5 or greater than or equal to 20, mixing the microporous parent zeolite with an aqueous metal hydroxide solution, and heating the microporous parent zeolite and aqueous metal hydroxide mixture to temperatures greater than or equal to 100° C. to produce the hierarchical mesoporous zeolite supports having an average pore size greater than 2 nm, greater than or equal to 5 nm, or even greater than or equal to 8 nm as determined using the BJH method. In some embodiments, the hierarchical mesoporous zeolite supports may be produced without a templating agent or a pore-directing agent.

As used in the present disclosure, microporous zeolites refer to zeolite particles that have an average pore size of less than 2 nm, such as less than 1 nm as determined using the BJH method. The microporous zeolites may have an average particle size, as measured by their longest dimension, of less than or equal to 100 nm. In some embodiments, the microporous parent zeolite particles are present as a single crystal structure. The microporous parent zeolites may have an average particle size from 1 nm to 800 nm, from 1 nm to 650 nm, from 1 nm to 500 nm, from 50 nm to 800 nm, from 100 nm to 800 nm, from 200 mm to 800 nm, from 200 nm to 500 nm, from 300 nm to 800 nm, or from 50 nm to 600 nm. The average particle size of a zeolite may refer to the average value of the particle size of all the particles of a zeolite in a given sample. In some embodiments, the microporous parent zeolite may have a molar ratio of silica to alumina ($SiO_2/Al_2O_3$) of at least 5, at least 15, at least 20, at least 25, at least 30, or even at least 35. In some embodiments, the microporous parent zeolite may have a molar ratio of silica to alumina of from 5 to 100, from 5 to 90, from 5 to 80, from 20 to 100, from 20 to 90, from 20 to 80, from 20 to 70, from 20 to 66, from 25 to 100, from 25 to 90, from 25 to 80, from 25 to 70, from 25 to 66, from 30 to 100, from 30 to 90, from 30 to 80, from 30 to 70, from 30 to 66, from 35 to 100, from 35 to 90, from 35 to 80, from 35 to 70, or even from 35 to 66.

In some embodiments, the microporous parent zeolite may be a beta zeolite. Providing the microporous parent zeolite may include synthesizing or preparing the microporous parent zeolites. Processes for preparing microporous parent zeolites may include, but are not limited to, synthesizing the microporous parent zeolites or directly acquiring the microporous parent zeolites from another source. It should be understood that multiple methods known in the art may be available to synthesize the microporous parent zeolites. In some embodiments, providing the microporous parent zeolites may include providing a colloidal mixture comprising the microporous parent zeolites, silica, alumina, and water.

Desilication methods for producing hierarchical mesoporous zeolite supports may further include contacting the microporous parent zeolites with an aqueous metal hydroxide solution. The aqueous metal hydroxide solution may include a single metal hydroxide species, or may be a combination of two or more metal hydroxide chemical species. In some embodiments, the aqueous metal hydroxide solution comprises at least one alkali metal hydroxide, at least one alkaline earth metal hydroxide, or combinations thereof. In other embodiments, the aqueous metal hydroxide solution may comprise LiOH, NaOH, KOH, RbOH, $Mg(OH)_2$, $Ca(OH)_2$, $Sr(OH)_2$, $Ba(OH)_2$, or combinations thereof. In some embodiments, contacting the microporous parent zeolite with the aqueous metal hydroxide solution may include mixing the combined mixture of the microporous parent zeolite and aqueous metal hydroxide.

The aqueous metal hydroxide solution may have a molar concentration of the metal hydroxide of from 0.01 moles per liter (M) to 10 M. In other embodiments, the aqueous metal hydroxide solution may have a molar concentration of the metal hydroxide of from 0.01 M to 5 M, from 0.01 M to 3 M, from 0.01 M to 1 M, from 0.05 M to 1 M, from 0.05 M to 0.8 M, from 0.05 M to 0.5 M, or even from 0.1 M to 0.4 M. In one or more embodiments, the combined mixture of the microporous parent zeolite and aqueous metal hydroxide may have a pH greater than or equal to 12 or even greater than or equal to 13. In some embodiments, the combined mixture of the microporous parent zeolite and aqueous metal hydroxide may have a pH of from 12 to 14 or even from 13 to 14.

The desilication methods for producing hierarchical mesoporous zeolite supports may further include heating the parent beta zeolite and aqueous metal hydroxide mixture. The heating may occur at temperatures greater than or equal to 100° C., greater than or equal to 125° C., greater than or equal to 150° C., greater than or equal to 175° C., or even greater than or equal to 200° C. The heating may occur at temperatures less than or equal to 500° C., less than or equal to 400° C., less than or equal to 300° C., or even less than or equal to 250° C. In some embodiments, the heating may occur at temperatures of from 100° C. to 500° C., from 125° C. to 500° C., from 150° C. to 500° C., from 175° C. to 500° C., from 200° C. to 500° C., from 250° C. to 500° C., from 100° C. to 400° C., from 100° C. to 300° C., from 100° C. to 250° C., from 125° C. to 300° C., from 150° C. to 300° C., or from 125° C. to 250° C. The parent beta zeolite and aqueous metal hydroxide mixture may be heated for a time interval of greater than or equal to 1 hour, greater than or equal to 4 hours, greater than or equal to 16 hours, greater than or equal to 18 hours, or even greater than or equal to 24 hours. In some embodiments, the parent beta zeolite and aqueous metal hydroxide mixture may be heated for a time interval of from 1 hour to 16 hours, from 4 hours to 16 hours, from 16 hours to 48 hours, from 16 hours to 30 hours, from 16 hours to 24 hours, from 18 hours to 48 hours, from 18 hours to 30 hours, from 18 hours to 24 hours, or from 24 hours to 48 hours. Following heating, the aqueous metal hydroxide mixture may be removed and the desilicated zeolite. The desilicated parent zeolite may be washed to remove excess metal hydroxide and may then be dried to produce the hierarchical mesoporous zeolite.

The desilication methods disclosed herein for producing the hierarchical mesoporous zeolite support may produce hierarchical mesoporous zeolite supports having an average pore size greater than 2 nm, greater than or equal to 4 nm, or even greater than or equal to 8 nm. As previously discussed, the average pore size of the hierarchical mesoporous zeolite support can be determine by Barrett-Joyner-Halenda (BJH) analysis. BJH analysis measures the amount of a gas (argon) that detaches from a material, such as the hierarchical mesoporous zeolite support, at 87 Kelvin over a range of pressures. Using the Kelvin equation, the average pore size of the material can be calculated from the amount of argon adsorbate removed from the pores of the material and the relative pressure of the system. The desilication methods may produce hierarchical mesoporous zeolite supports having an average pore size from 2 nm to 40 nm, from 2 nm to 30 nm, from 2 nm to 25 nm, from 5 nm to 40 nm, from 5 nm to 30 nm, from 5 nm to 25 nm, from 8 nm to 40 nm, from 8 nm to 30 nm, or from 8 nm to 25 nm, from 8 nm to 20 nm, from 10 nm to 25 nm, from 10 nm to 20 nm, from 12 nm to 25 nm, from 12 nm to 20 nm, from 8 nm to 18 nm, from 8 nm to 16 nm, or from 12 nm to 18 nm, as determined from BJH analysis.

The Non-Local Density Functional Theory (NLDFT) method can determine the total pore volume of the hierarchical mesoporous zeolite support from the adsorption data. The NLDFT method takes into account the rough surface area of crystalline silica materials. The desilication method may produce a hierarchical mesoporous zeolite support having a total pore volume greater than or equal to 0.35 cubic centimeters per gram ($cm^3/g$), greater than or equal to 0.4 $cm^3/g$, greater than or equal to 0.45 $cm^3/g$, or even greater than or equal to 0.5 $cm^3/g$, determined according to the NLDFT method.

Without intending to be limited by any particular theory, it is believed that upon contacting the microporous parent zeolite during the heating process, the metal hydroxide solution may create the mesopores by preferentially extracting silicon from the zeolite framework (also known as desilication). When the temperature is above 100° C. and the pressure is above ambient atmospheric pressure, the synthetic conditions become similar to the conventional bottom-up approach that favors crystallization of zeolites. During this desilication process, alumina present in the zeolite may aid in achieving hierarchical mesopore formation while preserving zeolite crystallinity. Not intending to be limited by any particular theory, it is believed that the alumina in the zeolite framework may prevent excessive silicon extraction by the metal hydroxide solution and may maintain a zeolite framework with locally-desilicated areas that can be recrystallized at the synthetic conditions. Therefore, the crystallinity of the resulting hierarchical mesoporous zeolite supports can be preserved during the formation of mesopores. The preservation of the crystallinity from the process may be verified by conducting X-Ray Diffraction (XRD) analysis of the hierarchical mesoporous zeolite support and the microporous parent zeolite and comparing the XRD plots for each. For a microporous parent zeolite exhibiting specific XRD peaks, a hierarchical mesoporous zeolite support produced from the microporous parent zeolite and having preserved crystallinity exhibits the same peaks and comparable peak intensities compared to the microporous parent zeolite. Maintaining the crystallinity of the hierarchical mesoporous zeolite support compared to the microporous parent zeolite may also preserve the acid reaction sites of the hierarchical mesoporous zeolite support compared to the microporous parent zeolite.

Although a desilication method for producing the hierarchical mesoporous zeolite support is described in detail, it is understood that any other process known in the art may also be used to produce the hierarchical mesoporous zeolite support. Methods for producing hierarchical mesoporous zeolite supports may include, but are not limited to, other "top down" methods conducted at temperatures less than 100° C., which may include utilizing pore-directing agents to facilitate formation of mesopores. "Top down" methods may refer to methods in which a parent zeolite is chemically eroded to produce the hierarchical mesoporous structure. Another method for producing hierarchical mesoporous zeolite supports may include "bottom up" methods, which include building up the hierarchical mesoporous zeolite from zeolite precursors. In the "bottom up" methods, templating agents are included and the zeolite is built-up around the templating agents to form the mesoporous structure. The resulting zeolite is then calcined to burn off the templating agent to produce the hierarchical mesoporous zeolite support. Other synthesis methods may also be used to produce the hierarchical mesoporous zeolite.

The multifunctional catalyst of the present disclosure for upgrading pyrolysis oil may be prepared from the hierarchical mesoporous zeolite support. The methods of preparing the multifunctional catalyst may include wet impregnation of at least a first metal catalyst precursor and a second metal catalyst precursor onto the outer surfaces, pore surfaces, or both, of the hierarchical mesoporous zeolite support. At least one of the first metal catalyst precursor, the second metal catalyst precursor, or both, is a heteropolyacid. The methods may include contacting the hierarchical mesoporous zeolite support with the solution that includes at least the first metal catalyst precursor, the second metal catalyst precursor, and a solvent. The solution may also, optionally, include a phosphorous-containing compound, such as when the heteropolyacid for the metal catalyst precursor does not include phosphorous.

The first metal catalyst precursor may include a first metal, and the second metal catalyst precursor may include a second metal different from the first metal. The first metal and the second metal may be transition metals, such as, but not limited to transition metals in Groups 5, 6, 7, 8, 9, and 10 of the International Union of Pure and Applied Chemistry (IUPAC) periodic table of elements. In some embodiments, the first metal of the first metal catalyst precursor may be a metal selected from cobalt, molybdenum, vanadium, or combinations of these. In some embodiments, the second metal of the second metal catalyst precursor may be a metal independently selected from cobalt, molybdenum, vanadium, or combinations of these, and may be different from the first metal.

The first metal catalyst precursor, the second metal catalyst precursor, or both may be a heteropolyacid. The heteropolyacid may include one or more than one metal selected from cobalt, molybdenum, or combinations of cobalt and molybdenum; at least one heteroatom selected from phosphorous (P), silicon (Si), arsenic (Ar), germanium (Ge), or combinations of these; and one or more than one acidic hydrogen. As used in this disclosure, the term "acidic hydrogen" may refer to a hydrogen atom of the heteropolyacid that may have a tendency to dissociate from the heteropolyacid in solution to form a positive ion. The heteropolyacid may also include oxygen. Heteropolyacids suitable for the first metal catalyst precursor, the second metal catalyst precursor, or both may have a Keggin structure having general formula $XM_{12}O_{40}{}^{n-}$ or a Dawson structure having the general formula $XM_{18}O_{82}{}^{n-}$, in which X is the heteroatom selected from phosphorous, silicon, arsenic, germanium, or combinations of these; M is the molybdenum and optionally one or more of cobalt, vanadium, or combinations of these; and n– is an integer indicative of the charge of the anion of the heteropolyacid. Examples of heteropolyacids may include, but are not limited to phosphormolybdic heteropolyacid ($H_3PMO_{12}O_{40}$), silicomolybdic heteropolyacid ($H_4SiMo_{12}O_{40}$), decamolybdiccobaltate heteropolyacid ($H_6[Co_2Mo_{10}O_{38}H_4]$), $H_4[PCoMO_{11}O_{40}]$, $H_4[PVMo_{11}O_{40}]$, $H_5[PV_2Mo_{10}O_{40}]$, $H_7[PV_4Mo_8O_{40}]$, $H_9[PV_6Mo_6O_{40}]$, $H_3[AsMo_{12}O_{40}]$, $H_4[AsCoMo_{11}O_{40}]$, $H_5[AsCo_2Mo_{10}O_{40}]$, $H_4[AsCoMo_{11}O_{40}]$, $H_5[AsCo_2Mo_{10}O_{40}]$, $H_4[AsVMo_{11}O_{40}]$, $H_5[AsVMo_{10}O_{40}]$, $H_7[AsV_4Mo_8O_{40}]$, $H_9[AsV_6Mo_6O_{40}]$, $H_5[SiCoMo_{11}O_{40}]$, $H_6[SiCO_2Mo_{10}O_{40}]$, $H_5[SiVMo_{11}O_{40}]$, $H_6[SiV_2Mo_{10}O_{40}]$, $H_{10}[SiV_6Mo_6O_{40}]$, $H_6[P_2Mo_{18}O_{82}]$, other heteropolyacids, salts of these heteropolyacids, or combinations of heteropolyacids. Salts of these heteropolyacids may include alkali metal salts, alkaline earth metal salts, nitrate salts, sulfate salts, or other salts of the heteropolyacid. Alkali metals may include sodium, potassium, rubidium, caesium, or combinations of these. Alkaline earth metals may include, but are not limited to magnesium, calcium, or combinations of these. In some embodiments, the heteropolyacid may include phosphormolybdic heteropolyacid having formula $H_3[PMo_{12}O_{40}]$. In some embodiments, the heteropolyacid may include decamolybdodicobaltate heteropolyacid having chemical formula $H_6[Co_2Mo_{10}O_{38}H_4]$. In some embodiments, the heteropolyacid may be silicomolybdic heterpolyacid having chemical formula $H_4[SiMo_{12}O_{40}]$. In some embodiments, the first metal catalyst precursor, the second catalyst precursor, or both may be a metal salt of a heteropolyacid, such as an alkali metal salt or alkaline metal salt of the heteropolyacid.

As previously described in this disclosure, the first metal catalyst precursor, the second metal catalyst precursor, or both may be a heteropolyacid. In some embodiments, the first metal catalyst precursor may include a heteropolyacid, and the second metal catalyst precursor may include a non-heteropolyacid precursor. In some embodiments, both the first metal catalyst precursor and the second metal catalyst precursor may include heteropolyacids. In some embodiments, the first metal catalyst precursor may include a first heteropolyacid, and the second metal catalyst precursor may include a second heteropolyacid that is different from the first heteropolyacid. For example, in some embodiments, the first metal catalyst precursor may include a first heteropolyacid that includes molybdenum as the metal, and the second metal catalyst precursor may include a second heteropolyacid that includes cobalt as the metal. In some embodiments, the first metal catalyst precursor and the second metal catalyst precursor may include the same heteropolyacid, and the heteropolyacid may include a first metal, a second metal that is different from the first metal, and at least one heteroatom. For example, in some embodiments, the solution may include decamolybdiccobaltate heteropolyacid having chemical formula $H_6[Co_2Mo_{10}O_{38}H_4]$, which includes both cobalt and molybdenum and may serve as both the first metal catalyst precursor and the second metal catalyst precursor.

In some embodiments, one of the first metal catalyst precursor or the second metal precursor may include a non-heteropolyacid metal catalyst precursor, such as a metallate hydrate, metal nitrate, and other non-heteropolyacid precursor. The solution may also include a phosphorous-containing compound, such as, but not limited to, phosphoric acid, phosphorous acid, or other phosphorous-containing compounds, such as when the heteroatom in the heteropolyacid is not phosphorous.

The first metal catalyst precursor and the second metal catalyst precursor may be dispersed or dissolved in a solvent to form the solution. The solvent may be water. The solvent may additionally include one or more organic solvents, such as but not limited to organic alcohols or other organic solvents. One or more than one of the heteropolyacids may be dehydrated prior to combining the heteropolyacid with the solvent to produce the solution. The solution may have a concentration of the first metal catalyst precursor sufficient to result in the first metal catalyst precursor being deposited on or adsorbed onto the outer surfaces and pore surfaces of the zeolite support. The solution may have greater than or equal to 1 wt. %, greater than or equal to 2 wt. %, greater than or equal to 5 wt. % or even greater than or equal to 10 wt. % first metal catalyst precursor based on the total weight of the solution before contact with the zeolite support. The solution may have less than or equal to 20 wt. %, less than or equal to 15 wt. %, or even less than or equal to 12 wt. % first metal catalyst precursor based on the total weight of the solution before contact with the zeolite support. In some embodiments, the solution may include from 1 wt. % to 20 wt. % of the first metal catalyst precursor, such as from 1 wt. % to 15 wt. %, from 1 wt. % to 10 wt. %, from 1 wt. % to 5 wt. %, from 2 wt. % to 20 wt. %, from 2 wt. % to 15 wt. %, from 2 wt. % to 10 wt. %, or from 2 wt. % to 5 wt. % first metal catalyst precursor based on the total weight of the solution before contact with the zeolite support.

The solution may have a concentration of the second metal catalyst precursor sufficient to result in the second metal catalyst precursor being deposited on or adsorbed onto the outer surfaces and pore surfaces of the zeolite support. The solution may have greater than or equal to 1 wt. %, greater than or equal to 2 wt. %, greater than or equal to 5 wt. % or even greater than or equal to 10 wt. % second metal catalyst precursor based on the total weight of the solution before contact with the zeolite support. The solution may have less than or equal to 20 wt. %, less than or equal to 15 wt. %, or even less than or equal to 12 wt. % second metal catalyst precursor based on the total weight of the solution before contact with the zeolite support. In some embodiments, the solution may include from 1 wt. % to 20 wt. % of the second metal catalyst precursor, such as from 1 wt. % to 15 wt. %, from 1 wt. % to 10 wt. %, from 1 wt. % to 5 wt. %, from 2 wt. % to 20 wt. %, from 2 wt. % to 15 wt. %, from 2 wt. % to 10 wt. %, or from 2 wt. % to 5 wt. % second metal catalyst precursor based on the total weight of the solution before contact with the zeolite support.

Once the solution is prepared, the hierarchical mesoporous zeolite support may be contacted with the solution at ambient conditions. The solution may be mixed for a period of time prior to contacting the hierarchical mesoporous zeolite support with the solution. The mixture comprising the hierarchical mesoporous zeolite support dispersed in the solution may be mixed for a period of time long enough to provide sufficient adsorption or deposition of the first metal catalyst precursor and the second metal catalyst precursor onto the outer surfaces and pore surfaces of the hierarchical mesoporous zeolite support. Contacting of the hierarchical mesoporous zeolite support with the solution containing the first metal catalyst precursor and the second metal catalyst precursor may result in a mixture of a multifunctional catalyst precursor dispersed in the solution. The mixture may also include the remaining first metal catalyst precursor, second metal catalyst precursor, and any other constituents that are not adsorbed onto the outer surfaces and pore surfaces of the zeolite support. The multifunctional catalyst precursor may include at least the first metal catalyst precursor and the second metal catalyst precursor deposited on or adsorbed onto the outer surfaces or pore surfaces of the hierarchical mesoporous zeolite support.

As previously discussed, after contacting the hierarchical mesoporous zeolite support with the solution comprising the first metal catalyst precursor and the second metal catalyst precursor, the excess liquids, such as solution or solvent, may be removed from the mixture to produce a multifunctional catalyst precursor. Removing the liquid components may include removing the excess solution from the multifunctional catalyst precursor and drying the multifunctional catalyst precursor. Removing the excess solution from the multifunctional catalyst precursor may include subjecting the mixture to decantation, filtration, vacuum filtration, or combinations of these. In some embodiments, removing the liquids from the mixture may include vacuum filtration of the mixture at a temperature of from 25° C. to 90° C. Drying the multifunctional catalyst precursor may include maintaining the multifunctional catalyst precursor at a temperature greater than or equal to the boiling temperature of the solvent, such as at a temperature of from 90° C. to 200° C. Drying may be conducted for a drying period sufficient to remove the solvent to a level of less than 1 wt. % of the total weight of the multifunctional catalyst precursor. The drying period may be from 1 hour to 24 hours, such as from 2 hours to 12 hours. Drying may remove additional solvent from the multifunctional catalyst through evaporation of the solvent. In some embodiments, the solvent may be water, and drying may include maintaining the multifunctional catalyst precursor at a temperature of greater than or equal to 100° C. for a drying period of greater than or equal to 1 hour.

As previously discussed, the method may further include calcining the multifunctional catalyst precursor to produce the multifunctional catalyst of the present disclosure. Calcining the multifunctional catalyst precursor may be conducted after removal of the excess solution and solvent from the multifunctional catalyst precursor. The multifunctional catalyst precursor may be calcined at a temperature of from 500° C. to 600° C. and for a calcination period of from 4 hours to 6 hours to produce the multifunctional catalyst.

The methods described in this disclosure are based on wet impregnation of the first and second catalyst precursors onto the outer surfaces and pore surfaces of the hierarchical mesoporous zeolite support. It is understood that other techniques known in the art may be employed to deposit the heteropolyacids and other metal catalyst precursors onto the outer surfaces and pore surfaces of the hierarchical mesoporous zeolite support to prepare the multifunctional catalyst.

The multifunctional catalyst for upgrading pyrolysis oil produced by the methods described in this disclosure may include at least a first metal catalyst and a second metal catalyst supported on the outer surfaces and pore surfaces of a hierarchical mesoporous zeolite support. The first metal catalyst and the second metal catalyst may include any of the metals previous previously described in this disclosure for the first metal catalyst and second metal catalyst, respectively. The multifunctional catalyst may also include the heteroatom from the heteropolyacid—such as but not limited to phosphorous, silicon, arsenic, germanium, or combinations of these—supported on the outer surfaces or pore surfaces of the zeolite support. In some embodiments, the first metal catalyst may be molybdenum and the second metal catalyst may be cobalt or vanadium, where at least the molybdenum is provided by the heteropolyacid. In some embodiments, the cobalt may also be provided by the same or a different heteropolyacid from the heteropolyacid that contributes the molybdenum. In some embodiments, the multifunctional catalyst may include molybdenum, cobalt, and phosphorous deposited on the outer surfaces and pore surfaces of a hierarchical mesoporous beta zeolite support, where at least the molybdenum and the phosphorous are provided by the heteropolyacid. In some embodiments, the multifunctional catalyst may include molybdenum, cobalt, and silicon deposited on the outer surfaces and pore surfaces of the hierarchical mesoporous beta zeolite support.

The use of a heteropolyacid for at least one of the metal catalyst precursors may reduce the acidity of the multifunctional catalyst compared to commercially available catalysts for upgrading pyrolysis oil prepared using conventional metal catalyst precursors. The multifunctional catalyst for upgrading pyrolysis oil of the present disclosure made using one or more than one heteropolyacid may have an acidity less than an acidity of an existing commercially available catalyst having the same metal catalyst species but made with conventional metal catalyst precursors. The multifunctional catalyst may have an acidity less than 15,000 micromoles of ammonia per gram ($\mu$mol($NH_3$)/g), less than or equal to 12,000, less than or equal to 10,000 $\mu$mol($NH_3$)/g, less than or equal to 9,000 $\mu$mol($NH_3$)/g, or less than or equal to 8,000 $\mu$mol($NH_3$)/g. In some embodiments, the multifunctional catalyst may have an acidity of from 1,000 $\mu$mol($NH_3$)/g to 15,000 $\mu$mol($NH_3$)/g, from 1,000 $\mu$mol($NH_3$)/g to 12,000 $\mu$mol($NH_3$)/g, from 1,000 $\mu$mol($NH_3$)/g to 10,000 $\mu$mol($NH_3$)/g, from 1,000 $\mu$mol($NH_3$)/g to 9,000 $\mu$mol($NH_3$)/g, or from 1,000 $\mu$mol($NH_3$)/g to 8,000 $\mu$mol($NH_3$)/g.

The multifunctional catalyst for upgrading pyrolysis oil of the present disclosure may have a BET surface area of greater than or equal to 300 meters squared per gram ($m^2/g$). As used herein, "BET surface area" refers to the average surface area of the metallic oxide particles as measured by the Brunauer Emmett Teller (BET) nitrogen absorption method according to ASTM D-6556 (American Society for Testing and Materials method D-6556). The multifunctional catalyst for upgrading pyrolysis oil of the present disclosure may have a BET surface area of greater than or equal to 310 $m^2/g$, greater than or equal to 320 $m^2/g$, or even greater than or equal to 350 $m^2/g$. The multifunctional catalyst for upgrading pyrolysis oil of the present disclosure may have a BET surface area of less than or equal to 700 $m^2/g$, less than or equal to 600 $m^2/g$, less than or equal to 500 $m^2/g$, or even less than or equal to 400 $m^2/g$. In some embodiments, the multifunctional catalyst for upgrading pyrolysis oil of the present disclosure may have a BET surface area of from 300 $m^2/g$ to 700 $m^2/g$, from 300 $m^2/g$ to 600 $m^2/g$, from 300 $m^2/g$ to 500 $m^2/g$, from 300 $m^2/g$ to 400 $m^2/g$, from 310 $m^2/g$ to 700 $m^2/g$, from 310 $m^2/g$ to 600 $m^2/g$, from 310 $m^2/g$ to 500 $m^2/g$, from 310 $m^2/g$ to 400 $m^2/g$, from 320 $m^2/g$ to 700 $m^2/g$, from 320 $m^2/g$ to 600 $m^2/g$, from 320 $m^2/g$ to 500 $m^2/g$, from 320 $m^2/g$ to 400 $m^2/g$, from 350 $m^2/g$ to 700 $m^2/g$, from 350 $m^2/g$ to 600 $m^2/g$, from 350 m²/g to 500 m²/g, from 350 m²/g to 400 m²/g, from 400 m²/g to 700 m²/g, from 400 m²/g to 600 m²/g, of from 400 m²/g to 500 m²/g.

In some embodiments, the multifunctional catalyst for upgrading pyrolysis oil may be a multifunctional catalyst produced by a process that may include contacting the hierarchical mesoporous zeolite support with the solution comprising at least the first metal catalyst precursor and the second metal catalyst precursor. The hierarchical mesoporous zeolite support may have an average pore size of from 2 nm to 40 nm as determined by BJH analysis. The hierarchical mesoporous zeolite support may have any other compositions, features, or characteristics previously described in this disclosure. The first metal catalyst precursor, the second metal catalyst precursor, or both, may include a heteropolyacid. Contacting the hierarchical mesoporous zeolite support with the solution may cause at least the first metal catalyst precursor and the second catalyst precursor to deposit onto outer surfaces and pore surfaces of the hierarchical mesoporous zeolite support to produce a multifunctional catalyst precursor. The solution, the first metal catalyst precursor, the second metal catalyst precursor, and one or more heteropolyacids may have any of the compositions, properties, or characteristics previously described in this disclosure for each of these, respectively. The method may further include removing the excess solution from the multifunctional catalyst precursor, and calcining the multifunctional catalyst precursor to produce the multifunctional catalyst. Each of the contacting step, removing excess solution step, and calcining step may be conducted under any of the process conditions previously described in this disclosure in relation to each of these process steps. The multifunctional catalyst produced by this method may include at least a first metal catalyst and a second metal catalyst deposited on the outer surfaces and the pore surfaces of the hierarchical mesoporous zeolite support. The multifunctional catalyst produced by the method may have any of the compositions, properties, or characteristics previously described in this disclosure for the multifunctional catalyst.

The multifunctional catalyst prepared by the methods described in this disclosure may be used to upgrade pyrolysis oil to produce one or more valuable aromatic intermediates, such as but not limited to benzene, toluene, ethylbenzene, xylenes, other aromatic compounds, or combinations of these. In some embodiments, a method for upgrading pyrolysis oil may include contacting the pyrolysis oil with the multifunctional catalyst at mild reaction conditions comprising reaction temperatures of less than 500° C. and pressures less than 6 MPa. The pyrolysis oil may have any of the compositions or characteristics previously described in this disclosure for pyrolysis oil. In some embodiments, the pyrolysis oil may include multi-ring aromatic compounds. The multifunctional catalyst may be prepared by any of the methods or processes for making the multifunctional catalyst described in this disclosure and may have any properties, compositions, or attributes described in this disclosure for the multifunctional catalyst. In some embodiments, the multifunctional catalyst may be produced by the process that includes contacting the hierarchical mesoporous zeolite support with the solution comprising at least the first metal catalyst precursor and the second metal catalyst precursor, the first metal catalyst precursor, the second metal catalyst precursor, or both, including a heteropolyacid. The hierarchical mesoporous zeolite support may have an average pore size of from 2 nm to 40 nm. The hierarchical mesoporous zeolite support, the solution, the first metal catalyst precursor, the second metal catalyst precursor, and one or more heteropolyacids may have any of the compositions, properties, or characteristics previously described in this disclosure for each of these, respectively. The contacting may cause at least the first metal catalyst precursor and the second catalyst precursor to deposit or be adsorbed onto the outer surfaces and pore surfaces of the hierarchical mesoporous zeolite support to produce a multifunctional catalyst precursor. The process for producing the multifunctional catalyst may include removing excess solution from the multifunctional catalyst precursor, and calcining the multifunctional catalyst precursor to produce the multifunctional catalyst. Each of the contacting step, removing excess solution step, and calcining step may be conducted under any of the process conditions previously described in this disclosure in relation to each of these process steps. The multifunctional catalyst may include a first metal catalyst and a second metal catalyst supported on the hierarchical mesoporous zeolite support.

Contact of the pyrolysis oil with the multifunctional catalyst at the reaction conditions may convert at least a portion of the multi-ring aromatic compounds in the pyrolysis oil to one or more C6-C8 aromatic compounds. The at least a portion of the multi-ring aromatic compounds converted to one or more C6-C8 compounds may include at least 30%, at least 40%, at least 50%, at least 60%, at least 70%, or at least 80% of the multi-ring aromatic compounds in the pyrolysis oil. The C6-C8 aromatic compounds may include, but are not limited to, one or more of benzene, toluene, ethylbenzene, xylene, or combinations of these. In some embodiments, contacting the pyrolysis oil with the multifunctional catalyst at the reactions conditions may convert the at least a portion of the multi-ring aromatic compounds in the pyrolysis oil to C6-C8 aromatic compounds in a single step, without conducting a subsequent chemical reaction step.

Contacting of the pyrolysis oil with the multifunctional catalyst may be conducted at a reaction temperature in a range comparable to the reaction temperatures for processes for upgrading pyrolysis oil using commercially-available catalysts prepared using conventional metal catalyst precursors. In some embodiments, the pyrolysis oil may be contacted with the multifunctional catalyst at a reaction temperature of less than or equal to 500° C., less than or equal to 450° C., or even less than or equal to 400° C. The pyrolysis oil may be contacted with the multifunctional catalyst at a reaction temperature of greater than or equal to 350° C., greater than or equal to 380° C. or even greater than or equal to 400° C. In some embodiments, pyrolysis oil may be contacted with the multifunctional catalyst at a reaction temperature of from 350° C. to 500° C., from 350° C. to 450° C., from 350° C. to 400° C., from 380° C. to 500° C., from 380° C. to 450° C., from 380° C. to 400° C., from 400° C. to 500° C., or from 400° C. to 425° C.

Contacting of the pyrolysis oil with the multifunctional catalyst may be conducted at a reaction pressure less than the reactions pressures necessary for upgrading pyrolysis oil using the commercially-available catalysts prepared using conventional metal catalyst precursors. Contacting of the pyrolysis oil with the multifunctional catalyst of the present disclosure may be conducted at a pressure that is 3 MPa to 5 MPa less than the reaction pressure required to upgrade pyrolysis oil using a conventional multi-metal catalyst. In some embodiments, the pyrolysis oil may be contacted with the multifunctional catalyst at a reaction pressure less than 6 MPa, less than or equal to 5 MPa, or even less than or equal to 4 MPa. In some embodiments, the pyrolysis oil may be contacted with the multifunctional catalyst at a reaction pressure greater than or equal to 0.1 MPa, greater than or equal to 1 MPa, or even greater than or equal to 2 MPa. In some embodiments, the pyrolysis oil may be contacted with the multifunctional catalyst at a reaction pressure of from 0.1 MPa to 5 MPa, from 0.1 MPa to 4 MPa, from 1 MPa to 5 MPa, from 1 MPa to 4 MPa, from 2 MPa to 5 MPa, or even from 2 MPa to 4 MPa.

In some embodiments, the method of upgrading pyrolysis oil may further include separating an upgraded pyrolysis oil from the multifunctional catalyst. Separating the upgraded pyrolysis oil from the multifunctional catalyst may be conducted using any known method or process of separating a fluid from a particulate solid.

Upgrading pyrolysis oil by contacting with the multifunctional catalyst of the present disclosure prepared from a hierarchical mesoporous zeolite support and including at least one metal catalyst derived from a heteropolyacid catalyst precursor may produce a greater yield of C6-C8 aromatic compounds, such as one or more than one of benzene, toluene, ethylbenzene, xylenes, or combinations of these, compared to upgrading the pyrolysis oil by contacting with commercially-available catalysts prepared using conventional metal catalyst precursors and microporous catalyst supports. In some embodiments, upgrading pyrolysis oil by contacting the pyrolysis oil with the multifunctional catalyst of the present disclosure prepared from a hierarchical mesoporous zeolite support using heteropolyacids may produce a combined yield of C6-C8 aromatic compounds of greater than or equal to 40 wt. %, greater than or equal to 45 wt. %, or even greater than or equal to 50 wt. %, based on the total weight of the upgraded pyrolysis oil separated from the multifunctional catalyst. Upgrading pyrolysis oil by contacting the pyrolysis oil with the multifunctional catalyst of the present disclosure prepared from a hierarchical mesoporous zeolite support using heteropolyacids may produce a combined yield of C6-C8 aromatic compounds that is at least 50% greater, at least 80% greater, or even at least 100% greater than a combined yield of C6-C8 aromatic compounds produced by contacting the pyrolysis oil with a multi-metal catalyst prepared from microporous catalyst supports and conventional metal catalyst precursors at the same temperature, pressure, and flow rates.

EXAMPLES

The following examples illustrate the methods of the present disclosure for producing multifunctional catalysts for upgrading pyrolysis oil and the methods for upgrading pyrolysis oil using the multifunctional catalysts. The Examples are not intended to limit the scope of the present disclosure in any way, in particular with respect to specific mass flow rates, stream compositions, temperatures, pressures, time on stream, amounts of catalytic metals on the zeolite support, or other variables fixed for the purposes of conducting the experiments.

Comparative Example 1: Comparative Catalyst for Upgrading Pyrolysis Oil

For Comparative Example 1, a comparative catalyst comprising a first catalyst metal and second catalyst metal deposited on the outer surfaces and pore surfaces of a nano-beta zeolite support was prepared using conventional metal precursors and no heteropolyacids. The first metal catalyst precursor was ammonium molybdate tetrahydrate having chemical formula $[(NH_3)_6Mo_7O_{24}.4H_2O]$, which was obtained from Sigma-Aldrich. The second metal catalyst precursor was cobalt (II) nitrate hexahydrate having chemical formula $[Co(NO_3)_2.6H_2O]$, which was also obtained from Sigma-Aldrich. The nano-beta zeolite catalyst support for Comparative Example 1 was CP814E nano-beta zeolite obtained from Zeolyst International. The nano-beta zeolite support particles had a ratio of the molar amount of silica $(SiO_2)$ divided by the molar amount of alumina $(Al_2O_3)$ of 25 (Beta-N).

The comparative catalyst of Comparative Example 1 was produced by adding 10 grams of the nano-beta zeolite catalyst support (Beta-N) to a round bottom flask. A Solution A was prepared by dissolving 3.08 grams of $[(NH_3)_6Mo_7O_{24}.4H_2O]$ in 50 milliliters (mL) of distilled water. A Solution B was then prepared by dissolving 2.65 grams of the $[Co(NO_3)_2.6H_2O]$ in 50 mL of distilled water. The amounts of $[(NH_3)_6Mo_7O_{24}.4H_2O]$ and $[Co(NO_3)_2.6H_2O]$ were selected to provide a final metal loading in the comparative catalyst of Comparative Example 1 of 3 wt. % Co and 12 wt. % Mo, respectively. Solution A and Solution B were then mixed together and added to Beta-N support in the round bottom flask. The combined solution and the Beta-N support were mixed for 2 hours. The water was removed from the Beta-N support impregnated with the first and second metal catalyst precursors under vacuum at a temperature of 50° C., and the solid sample was dried overnight at a temperature of 100° C. The solid sample was then calcined at a temperature of 500° C. for five hours to obtain the comparative catalyst of Comparative Example 1.

Comparative Example 2: Comparative Phosphorous-Containing Catalyst for Upgrading Pyrolysis Oil For Comparative Example 2, a comparative phosphorous-containing catalyst comprising a first catalyst metal, second catalyst metal, and phosphorous deposited on the outer surfaces and pore surfaces of the Beta-N support was prepared using conventional metal precursors and no heteropolyacids. The first metal catalyst precursor was ammonium molybdate tetrahydrate having chemical formula $[(NH_3)_6Mo_7O_{24}.4H_2O]$, which was obtained from Sigma-Aldrich. The second metal catalyst precursor was cobalt (II) nitrate hexahydrate having chemical formula $[Co(NO_3)_2.6H_2O]$, which was also obtained from Sigma-Aldrich. The Beta-N support was the nano-beta zeolite catalyst support previously described in Comparative Example 1. Phosphoric acid $(H_3PO_4)$ obtained from Sigma-Aldrich was used to incorporate the phosphorous.

The comparative phosphorous-containing catalyst of Comparative Example 2 was produced by adding 10 grams of the Beta-N support to a round bottom flask. A Solution A was prepared by dissolving 3.08 grams of the first metal catalyst precursor $[(NH_3)_6Mo_7O_{24}.4H_2O]$ in 50 milliliters (mL) of distilled water. A Solution B was then prepared by dissolving 2.65 grams of the second metal catalyst precursor $[Co(NO_3)_2.6H_2O]$ in 50 mL of distilled water. The amounts of $[(NH_3)_6Mo_7O_{24}.4H_2O]$ and $[Co(NO_3)_2.6H_2O]$ were selected to provide a final metal loading in the comparative catalyst of Comparative Example 2 of 3 wt. % Co and 12 wt. % Mo, respectively. Solution A and Solution B were then mixed together, and 0.15 grams of phosphoric acid was dissolved in the combined solution to produce Solution C. Solution C was then added to the Beta-N support in the round bottom flask and mixed for 2 hours. The water was removed from the Beta-N support impregnated with the first and second metal catalyst precursors under vacuum at a temperature of 50° C., and the solid sample was dried overnight at a temperature of 100° C. The solid sample was then calcined at a temperature of 500° C. for five hours to obtain the comparative phosphorous-containing catalyst of Comparative Example 2.

Example 3: Multifunctional Catalyst for Upgrading Pyrolysis Oil Prepared Using a Heteropolyacid In Example 3, a multifunctional catalyst comprising a first metal catalyst, a second metal catalyst, and phosphorous deposited on the outer surfaces and pore surfaces of the Beta-N support was prepared using a heteropolyacid for first metal catalyst precursor and the phosphorous. The first metal catalyst precursor was phosphormolybdic heteropolyacid having chemical formula $[H_3PMo_{12}O_{40}]$, which was obtained from Sigma-Aldrich. The second metal catalyst precursor was cobalt (II) nitrate hexahydrate having chemical formula $[Co(NO_3)_2 \cdot 6H_2O]$, which was also obtained from Sigma-Aldrich. The Beta-N support was the nano-beta zeolite catalyst support previously described in Comparative Example 1.

The multifunctional catalyst of Example 3 was produced by adding 10 grams of the Beta-N support to a round bottom flask. Solution A was prepared by dissolving 2.89 grams of the heteropolyacid of the first metal catalyst precursor $[H_3PMo_{12}O_{40}]$ in 50 milliliters (mL) of distilled water. Solution B was then prepared by dissolving 2.24 grams of the second metal catalyst precursor $[Co(NO_3)_2 \cdot 6H_2O]$ in 50 mL of distilled water. The amounts of the first metal catalyst precursor and second metal catalyst precursor were calculated to provide the same metal loading as the comparative catalysts of Comparative Examples 1 and 2 (3 wt. % Co and 12 wt. % Mo). Solution A and Solution B were then mixed together and added to the Beta-N support in the round bottom flask. The combined solution and the Beta-N support were mixed for 2 hours. The water was removed from the Beta-N support impregnated with the first and second metal catalyst precursors under vacuum at a temperature of 50° C., and the resulting multifunctional catalyst precursor was dried overnight at a temperature of 100° C. The dried multifunctional catalyst precursor was then calcined at a temperature of 500° C. for five hours to obtain the multifunctional catalyst of Example 3.

Example 4: Multifunctional Catalyst for Upgrading Pyrolysis Oil Prepared Using a Hierarchical Mesoporous Beta Zeolite Support In Example 4, the multifunctional catalyst for uprading pyrolysis oil was prepared by first upgrading the zeolite support to a hierarchical mesoporous zeolite support. The first metal catalyst, second metal catalyst, and phosphorous were then deposited on the outer surfaces and pore surface of the hierarchical mesoporous zeolite support using a heteropolyacid for the first metal catalyst precursor and phosphorous.

The starting beta zeolite was HSZ-931 HOA beta zeolite obtained from Tosoh, which is a micrometer-sized beta zeolite having a molar ratio of silica to alumina ($SiO_2/Al_2O_3$) of 28. The beta zeolite was converted to hierarchical mesoporous beta zeolite by adding 22.2 grams of the HSZ-931 HOA beta zeolite to 600 mL of a 0.2 molar (M) solution of NaOH. The mixture was then subjected to hydrothermal desilication at a temperature of 150° C. for 21 hours. The hierarchical mesoporous beta zeolite had a final molar ratio of silica to alumina after the conversion of 20. The hierarchical mesoporous beta zeolite had an average pore size of 10 nm with a peak pore size in the range of 20-25 nm, as determined by the methods previously discussed in this disclosure. The hierarchical mesoporous beta zeolite also had a pore volume of 0.59 cubic centimeters per gram.

The acidity of the hierarchical mesoporous beta zeolite was adjusted by dealumination in a diluted nitric acid solution. In particular, for Example 4, the hierarchical mesoporous beta zeolite was dealimunated by contacting the hierarchical mesoporous beta zeolite with a 0.2 M solution of nitric acid ($HNO_3$) at 80° C. for a period of 2 hours. The dealuminated hierarchical mesoporous beta zeolite was then ion-exchanged in a 0.8 M solution of ammonium nitrate ($NH_4NO_3$) for 2 hours at 80° C. one time. The ion-exchanged dealuminated hierarchical mesoporous beta zeolite was then dried and calcined at 550° C. for 5 hours to produce the hierarchical mesoporous beta zeolite support of Example 4, which is referred to in this disclosure as Beta-M50 zeolite support.

The multifunctional catalyst of Example 4 was then produced by adding 5 grams of the Beta-M50 zeolite support to a round bottom flask. Solution A was prepared by dissolving 1.44 grams of the heteropolyacid of the first metal catalyst precursor $[H_3PMo_{12}O_{40}]$ in 15 mL of distilled water. Solution B was then prepared by dissolving 1.12 grams of the second metal catalyst precursor $[Co(NO_3)_2 \cdot 6H_2O]$ in 15 mL of distilled water. The amounts of the first metal catalyst precursor and second metal catalyst precursor were calculated to provide the same metal loading as the comparative catalysts of Comparative Examples 1 and 2 and the multifunctional catalyst of Example 3 (3 wt. % Co and 12 wt. % Mo). Solution A and Solution B were then mixed together and added to the Beta-M50 zeolite support in the round bottom flask. The combined solution and the Beta-M50 zeolite support were mixed for 2 hours. The water was removed from the Beta-M50 zeolite support impregnated with the first and second metal catalyst precursors under vacuum at a temperature of 50° C., and the resulting multifunctional catalyst precursor was dried overnight at a temperature of 100° C. The dried multifunctional catalyst precursor was then calcined at a temperature of 500° C. for five hours to obtain the multifunctional catalyst of Example 4.

Example 5: Upgrading Pyrolysis Oil

In Example 5, the comparative catalysts of Comparative Examples 1 and 2 and the multifunctional catalyst of Examples 3 and 4 were used to upgrade a model pyrolysis oil composition to produce at least benzene, toluene, ethylbenzene, and xylene. 1-methylnaphthalene obtained from Sigma-Aldrich was used as the model pyrolysis oil.

Referring to FIG. 3, the apparatus 100 in which the model pyrolysis oil upgrading was conducted is schematically depicted. The apparatus 100 included a fixed bed reactor 110 with the catalyst loaded in zone 111. The fixed bed reactor 110 was maintained in a hot box 112 to maintain the fixed bed reactor 110 at constant temperature. The liquid feed 116, which included the model pyrolysis oil (1-methylnaphthalene) was introduced to the fixed bed reactor 110 using a liquid pump 120. Hydrogen 118 and nitrogen 119 can also be added to the liquid feed 116 upstream of the fixed bed reactor 110. The liquid feed 116 was passed through a heat exchanger 130 to adjust a temperature of the liquid feed 116 before passing it to the fixed bed reactor 110. The liquid feed 116 was contacted with the catalyst in the fixed bed reactor 110, the contacting causing reaction of at least the model pyrolysis oil (1-methylnaphthalene) to upgrade the model pyrolysis oil to produce a liquid product stream 114 comprising at least benzene, toluene, ethylbenzene, and xylene. The operating conditions of the fixed bed reactor 110 are listed in Table 1.

catalysts of Comparative Examples 1 and 2 and Examples 3 and 4 are provided subsequently in Table 1. The yields for each of the constituents in Table 1 are provided in weight percent based on the total mass flow rate of the liquid product stream 114.

TABLE 1

Results of Upgrading of Model Pyrolysis Oil with the Comparative Catalysts of Comparative Examples 1 and 2 and the Multifunctional Catalysts of Examples 3 and 4

|  | Comparative Example 1 | Comparative Example 2 | Example 3 | Example 4 |
|---|---|---|---|---|
| Catalyst Support | Nano-beta zeolite | Nano-beta zeolite | Nano-beta zeolite | Beta-M50 |
| First Metal Catalyst Precursor | $(NH_3)_6Mo_7O_{24} \cdot 4H_2O$ | $(NH_3)_6Mo_7O_{24} \cdot 4H_2O$ | $H_3PMo_{12}O_{40}$ | $H_3PMo_{12}O_{40}$ |
| Second Metal Catalyst Precursor | $Co(NO_3)_2 \cdot 6H_2O$ | $Co(NO_3)_2 \cdot 6H_2O$ | $Co(NO_3)_2 \cdot 6H_2O$ | $Co(NO_3)_2 \cdot 6H_2O$ |
| Phosphorous Source | N/A | $H_3PO_4$ | $H_3PMo_{12}O_{40}$ | $H_3PMo_{12}O_{40}$ |
| Catalyst Acidity ($\mu mol(NH_3)/g$) | 4703.6 | 14570.0 | 3258.8 | 8786.1 |
| Catalyst BET Surface Area ($m^2/g$) | 329.104 | 320.730 | 350.632 | 368.521 |
| Reaction Temperature (° C.) | 400 | 400 | 400 | 400 |
| Weight Hourly Space Velocity (hour$^{-1}$) | 1.2 | 1.2 | 1.2 | 1.2 |
| Total Pressure (MPa) | 3 | 3 | 3 | 3 |
| Total Conversion of 1-methylnaphthalene (%) | 86.1 | 81.8 | 86.7 | 94.3 |
| Time on Stream (hour) | 20 | 20 | 20 | 20 |
| Benzene Yield (wt. %) | 4.60 | 4.36 | 6.25 | 10.24 |
| Toluene Yield (wt. %) | 12.96 | 11.75 | 17.64 | 26.59 |
| Ethylbenzene Yield (wt. %) | 2.47 | 2.22 | 3.71 | 4.37 |
| Total Xylene Yield (wt. %) | 7.30 | 5.68 | 9.27 | 16.80 |
| Para-Xylene Yield (wt. %) | 1.78 | 1.40 | 2.28 | 4.02 |
| Meta-Xylene Yield (wt. %) | 3.83 | 2.99 | 4.86 | 8.97 |
| Ortho-Xylene Yield (wt. %) | 1.69 | 1.29 | 2.13 | 3.81 |
| C(3-4)-Benzene* Yield (wt. %) | 15.02 | 9.09 | 14.44 | 15.36 |
| Tetralin Yield (wt. %) | 0.60 | 0.23 | 0.34 | 0.17 |
| Naphthalene Yield (wt. %) | 2.53 | 2.31 | 2.92 | 2.05 |
| Methyltetralin Yield (wt. %) | 12.91 | 23.61 | 19.71 | 11.28 |
| Other 2-Ar (wt. %) | 8.89 | 7.32 | 7.36 | 3.82 |
| Total BTEX Yield** (wt. %) | 27.3 | 24.0 | 36.7 | 58.0 |

*C(3-4)-Benzene refers to benzene substituted with one or more alkyl group for which the total number of carbon atoms in the alkyl group is 3 or 4.
**Total BTEX Yield refers to the total combined yield of benzene, toluene, ethylbenzene, and xylenes (para-xylene, meta-xylene, and ortho-xylene).

The liquid product stream 114 was passed from the fixed bed reactor 110 to a liquid gas separator 140, in which the liquid product stream 114 was separated into a gaseous fraction 142 comprising the lesser boiling temperature constituents and a liquid fraction 144 comprising the greater boiling point fractions and unreacted model pyrolysis oil (1-methylnaphthalene). The liquid fraction 144 was analyzed for composition. The gaseous fraction 142 was passed to an online gas chromatograph for analysis of the composition of the gaseous fraction 142. The compositions of the gaseous fraction 142 and liquid fraction 144 were then used to determine the yield for each of the constituents of the liquid product stream 114. The yields for each of the compounds produced in the fixed bed reactor for each of the As shown in Table 1, the multifunctional catalyst of Example 4 provided the best performance for upgrading the model pyrolysis oil (1-methylnaphthalene) to benzene, toluene, ethylbenzene, and xylenes (BTEX). The total BTEX yield obtained using the multifunctional catalyst of Example 4 was 58 wt. %, which is greater than 2 times the yield of BTEX obtained with the comparative catalysts of Comparative Examples 1 and 2, which comprise catalyst made with conventional metal catalyst precursors deposited on a nano-beta zeolite support. The multifunctional catalyst of Example 4 prepared using the Beta-M50 hierarchical mesoporous beta zeolite support resulted in a 58% increase in the total yield of BTEX compared to the multifunctional catalyst of Example 3, which was prepared using a heteropolyacid but included the nano-beta zeolite support. The multifunctional catalyst of Example 4 also resulted in the greatest overall conversion of 1-methylnaphthalene at 94.3% conversion. Thus, at the same temperature and pressure, the multifunctional catalyst of Example 4 that includes a hierarchical mesoporous beta zeolite support may provide greater yield of BTEX compared to conventional catalysts such as the comparative catalysts of Comparative Examples 1 and 2.

Example 6: Effect of Acidity of Hierarchical Mesoporous Zeolite on Performance of the Multifunctional Catalyst In Example 6, the effects of changing the acidity of the hierarchical mesoporous beta zeolite support on the performance of the multifunctional catalysts were studied. For Example 6, the starting beta zeolite was the HSZ-931 HOA beta zeolite obtained from Tosoh, which is a micrometer-sized beta zeolite having a molar ratio of silica to alumina ($SiO_2/Al_2O_3$) of 28. The beta zeolite was converted to hierarchical mesoporous beta zeolite by adding 22.2 grams of the HSZ-931 HOA beta zeolite to 600 mL of a 0.2 molar (M) solution of NaOH. The mixture was then subjected to hydrothermal desilication at a temperature of 150° C. for 21 hours. The hierarchical mesoporous beta zeolite had a final molar ratio of silica to alumina after the conversion of 20. The hierarchical mesoporous beta zeolite had an average pore size of 10 nm with a peak pore size in the range of 20-25 nm, as determined by the methods previously discussed in this disclosure. The hierarchical mesoporous beta zeolite also had a pore volume of 0.59 cubic centimeters per gram.

For Sample 6A, the acidity was not adjusted. Instead, the hierarchical mesoporous beta zeolite of Sample 6A was subjected to ion-exchange in a 0.8 M solution of $NH_4NO_3$ for 2 hours at 80° C. three times, dried, and calcined at 550° C. for 5 hours. The hierarchical mesoporous beta zeolite support of Sample 6A is referred to in this disclosure as Beta-M20 zeolite support.

For Samples 6B, 6C, and 6D, the acidity of the hierarchical mesoporous beta zeolite was adjusted by dealumination in a diluted nitric acid solution. For each of Samples 6B, 6C, and 6D, the hierarchical mesoporous beta zeolite was dealuminated by contacting the hierarchical mesoporous beta zeolite with a solution of nitric acid ($HNO_3$) at 80° C. for a period of 2 hours. The concentrations of $HNO_3$ in the solutions were 0.15 M, 0.2 M, and 0.25 M for Samples 6B, 6C, and 6D, respectively. Each of the dealuminated hierarchical mesoporous beta zeolites of Samples 6B, 6C, and 6D were then ion-exchanged in a 0.8 M solution of $NH_4NO_3$ for 2 hours at 80° C. one time. The ion-exchanged dealuminated hierarchical mesoporous beta zeolite were then dried and calcined at 550° C. for 5 hours to produce the hierarchical mesoporous beta zeolite support of Samples 6B, 6C, and 6D, which are referred to in this disclosure as Beta-M35, Beta-M50, and Beta-M66, respectively.

The hierarchical mesoporous beta zeolite supports of Samples 6A, 6B, 6C, and 6D were evaluated for average pore size (average diameter), BET surface area ($S_{BET}$), external surface area ($S_{ext}$), micropore volume ($V_{mic}$), total pore volume ($V_T$), total acidity, and maximum desorption temperature ($T_{max}$), which are provided subsequently in Table 2. The external surface area ($S_{ext}$) was determined using the t-plot method, which is well-known in the art. The micropore volume ($V_{mic}$) and total pore volume ($V_T$) were determined by the NLDFT method previously discussed in this disclosure.

TABLE 2

Properties of Hierarchical Mesoporous Beta Zeolite Supports for Example 6

| Sample | 6A | 6B | 6C | 6D |
|---|---|---|---|---|
| Silica/Alumina Ratio | 20 | 35 | 50 | 66 |
| Average pore size (nm) | 9.9 | 9.8 | 9.9 | 10.3 |
| $S_{BET}$ (m²/g) | 611 | 611 | 608 | 609 |
| $S_{ext}$ (m²/g) | 197 | 205 | 197 | 196 |
| $V_{mic}$ (cm³/g) | 0.28 | 0.28 | 0.27 | 0.27 |
| $V_T$ (cm³/g) | 0.58 | 0.59 | 0.59 | 0.60 |
| Total Acidity (mmol/g) | 0.79 | 0.70 | 0.54 | 0.36 |
| $T_{max}$ (° C.) | 313 ± 2 | 340 ± 5 | 347 ± 3 | 330 ± 3 |

The multifunctional catalysts of Example 6 (Catalysts 6A-6D) were prepared from the Beta-M20, Beta-M35, Beta-M50, and Beta-M66 zeolite supports using the heteropolyacid according to the method previously described in Example 4. The multifunctional catalysts of Example 6 were then used to upgrade a model pyrolysis oil using the apparatus and methods previously described in Example 5. The yields of each of the compounds produced in the fixed bed reactor for each of the catalysts of Example 6 are provided in Table 3. The yields for each of the constituents in Table 3 are provided in weight percent based on the total mass flow rate of the liquid product stream.

TABLE 3

Results of Upgrading of Model Pyrolysis Oil with the Catalysts of Example 6

|  | 6A | 6B | 6C | 6D |
|---|---|---|---|---|
| Catalyst Support | Beta-M20 | Beta-M35 | Beta-M50 | Beta-M66 |
| First Metal Catalyst Precursor | $H_3PMo_{12}O_{40}$ | $H_3PMo_{12}O_{40}$ | $H_3PMo_{12}O_{40}$ | $H_3PMo_{12}O_{40}$ |
| Second Metal Catalyst Precursor | $Co(NO_3)_2 \cdot 6H_2O$ | $Co(NO_3)_2 \cdot 6H_2O$ | $Co(NO_3)_2 \cdot 6H_2O$ | $Co(NO_3)_2 \cdot 6H_2O$ |
| Phosphorous Source | $H_3PMo_{12}O_{40}$ | $H_3PMo_{12}O_{40}$ | $H_3PMo_{12}O_{40}$ | $H_3PMo_{12}O_{40}$ |
| Catalyst Acidity ($\mu mol(NH_3)/g$) | 10252.8 | 9438.0 | 8786.1 | 7879.1 |
| Catalyst BET Surface Area (m²/g) | 357.144 | 353.125 | 368.521 | 317.013 |
| Reaction Temperature (° C.) | 400 | 400 | 400 | 400 |
| Weight Hourly Space Velocity (hour⁻¹) | 1.2 | 1.2 | 1.2 | 1.2 |
| Total Pressure (MPa) | 3 | 3 | 3 | 3 |

TABLE 3-continued

Results of Upgrading of Model Pyrolysis Oil with the Catalysts of Example 6

|  | 6A | 6B | 6C | 6D |
|---|---|---|---|---|
| Total Conversion of 1-methylnaphthalene (%) | 79.9 | 92.2 | 94.3 | 94.5 |
| Time on Stream (hour) | 20 | 20 | 20 | 20 |
| Benzene Yield (wt. %) | 7.90 | 10.18 | 10.24 | 9.93 |
| Toluene Yield (wt. %) | 20.45 | 25.47 | 26.59 | 26.24 |
| Ethylbenzene Yield (wt. %) | 3.39 | 4.27 | 4.37 | 4.73 |
| Total Xylene Yield (wt. %) | 11.99 | 16.05 | 16.80 | 15.64 |
| Para-Xylene Yield (wt. %) | 2.89 | 3.84 | 4.02 | 3.79 |
| Meta-Xylene Yield (wt. %) | 6.39 | 8.60 | 8.97 | 8.31 |
| Ortho-Xylene Yield (wt. %) | 2.71 | 3.61 | 3.81 | 3.54 |
| C(3-4)-Benzene* Yield (wt. %) | 12.18 | 13.91 | 15.36 | 17.07 |
| Tetralin Yield (wt. %) | 0.22 | 0.16 | 0.17 | 0.27 |
| Naphthalene Yield (wt. %) | 1.91 | 1.63 | 2.05 | 2.44 |
| Methyltetralin Yield (wt. %) | 11.89 | 9.74 | 11.28 | 11.37 |
| Other 2-Ar (wt. %) | 4.58 | 3.26 | 3.82 | 5.14 |
| Total BTEX Yield** (wt. %) | 43.7 | 56.0 | 58.0 | 56.5 |

*C(3-4)-Benzene refers to benzene substituted with one or more alkyl group, for which the total number of carbon atoms in the alkyl group is 3 or 4.
**Total BTEX Yield refers to the total combined yield of benzene, toluene, ethylbenzene, and xylenes (para-xylene, meta-xylene, and ortho-xylene).

As shown in Table 3, the inclusion of the hierarchical mesoporous beta zeolite support produes a combined yield of BTEX of at least 40 wt. % regardless of the ratio of silica to alumina ($SiO_2/Al_2O_3$) in the hierarchical mesoporous beta zeolite support, for $SiO_2/Al_2O_3$ between about 20 and about 66 (Beta-M20 and Beta-M66). However, when the proportion of alumina is decreased so that the ratio $SiO_2/Al_2O_3$ is at least about 35, the combined yield of BTEX produced through contact of the multifunctional catalyst with the pyrolysis oil increases to 56 wt. %. The combined yield of BTEX is greatest for Sample 6C, for which the hierarchical mesoporous beta zeolite support was Beta-M50 having a $SiO_2/Al_2O_3$ of about 50. At a $SiO_2/Al_2O_3$ of 66 in Sample 6D, the combined yield of BTEX decreases again to 56 wt. %. This indicates that removal of too much alumina (for example, at a $SiO_2/Al_2O_3$ greater than 66) may lead to reduced activity of the multifunctional catalyst for upgrading pyrolysis oil to BTEX.

In a first aspect of the present disclosure, a method of making a multifunctional catalyst for upgrading pyrolysis oil can include contacting a hierarchical mesoporous zeolite support with a solution comprising at least a first metal catalyst precursor and a second metal catalyst precursor. The hierarchical mesoporous zeolite support may have an average pore size of from 2 nanometers to 40 nanometers as determined by Barrett-Joyner-Halenda (BJH) analysis, the first metal catalyst precursor, the second metal catalyst precursor, or both, comprises a heteropolyacid, and the contacting deposits the first metal catalyst precursor and the second catalyst precursor onto outer surfaces and pore surfaces of the hierarchical mesoporous zeolite support to produce a multifunctional catalyst precursor. The method may further include removing excess solution from the multifunctional catalyst precursor and calcining the multifunctional catalyst precursor to produce the multifunctional catalyst comprising at least a first metal catalyst and a second metal catalyst deposited on the outer surfaces and pore surfaces of the hierarchical mesoporous zeolite support.

A second aspect of the present disclosure is directed to a multifunctional catalyst for upgrading pyrolysis oil, where the multifunctional catalyst is produced by a process that includes contacting a hierarchical mesoporous zeolite support with a solution comprising at least a first metal catalyst precursor and a second metal catalyst precursor. The hierarchical mesoporous zeolite support may have an average pore size of from 2 nanometers to 40 nanometers as determined by Barrett-Joyner-Halenda (BJH) analysis, the first metal catalyst precursor, the second metal catalyst precursor, or both, comprises a heteropolyacid, and the contacting deposits the first metal catalyst precursor and the second catalyst precursor onto outer surfaces and pore surfaces of the hierarchical mesoporous zeolite support to produce a multifunctional catalyst precursor. The process may further include removing excess solution from the multifunctional catalyst precursor and calcining the multifunctional catalyst precursor to produce the multifunctional catalyst. The multifunctional catalyst may include at least a first metal catalyst and a second metal catalyst deposited on the outer surfaces and the pore surfaces of the zeolite support.

A third aspect of the present disclosure may include either of the first or second aspects, in which the hierarchical mesoporous zeolite support comprises a hierarchical mesoporous beta zeolite support.

A fourth aspect of the present disclosure may include any of the first through third aspects, in which the hierarchical mesoporous zeolite support has an average pore size of from 5 nanometers to 25 nanometers as determined by BJH analysis.

A fifth aspect of the present disclosure may include any of the first through fourth aspects, in which the hierarchical mesoporous zeolite support has a total pore volume of greater than or equal to 0.35 cubic centimeters per gram.

A sixth aspect of the present disclosure may include any of the first through fifth aspects, in which the hierarchical mesoporous zeolite support comprises a molar ratio of silica to alumina of from 20 to 100.

A seventh aspect of the present disclosure may include any of the first through sixth aspects, in which the method or process further comprises producing the hierarchical mesoporous zeolite support.

An eighth aspect of the present disclosure may include the seventh aspect, in which producing the hierarchical mesoporous zeolite support may comprise converting a microporous parent zeolite into the hierarchical mesoporous zeolite support through desilication of the microporous parent zeolite.

A ninth aspect of the present disclosure may include the eighth aspect, in which desilication of the microporous parent zeolite to produce the hierarchical mesoporous zeolite support may include mixing the microporous zeolite with an aqueous metal hydroxide solution and heating the microporous zeolite and aqueous metal hydroxide mixture to a temperature of greater than or equal to 100 degrees Celsius to produce the hierarchical mesoporous zeolite support.

A tenth aspect of the present disclosure may include any of the first through ninth aspects, in which the heteropolyacid may include at least one metal selected from cobalt, molybdenum, vanadium, or combinations of these metals and at least one heteroatom selected from phosphorous, silicon, arsenic, or combinations of these heteroatoms.

An eleventh aspect of the present disclosure may include any of the first through tenth aspects, in which the first metal catalyst precursor comprises the heteropolyacid.

A twelfth aspect of the present disclosure may include any of the first through eleventh aspects, in which the first metal catalyst precursor comprises a first heteropolyacid and the second metal catalyst precursor comprises a second heteropolyacid that is different from the first heteropolyacid.

A thirteenth aspect of the present disclosure may include the twelfth aspect, in which the first heteropolyacid or the second heteropolyacid is $H_3PMo_{12}O_{40}$.

A fourteenth aspect of the present disclosure may include any of the first through eleventh aspects, in which the heteropolyacid comprises phosphormolybdic heteropolyacid having formuala $H_3PMo_{12}O_{40}$.

A fifteenth aspect of the present disclosure may include any of the first through eleventh aspects, in which the first metal catalyst precursor and the second metal catalyst precursor are the same heteropolyacid, and the heteropolyacid comprises a first metal, a second metal that is different from the first metal, and at least one heteroatom.

A sixteenth aspect of the present disclosure may include the fifteenth aspect, in which the heteropolyacid comprises decamolybdodicobaltate heteropolyacid having chemical formula $H_6[Co_2Mo_{10}O_{38}H_4]$.

A seventeenth aspect of the present disclosure may include any of the first through sixteenth aspects, in which the multifunctional catalyst precursor is calcined at a temperature of 400 degrees Celsius to 700 degrees Celsius and for a time of from 4 hours to 6 hours to produce the multifunctional catalyst.

An eighteenth aspect of the present disclosure may include any of the first through seventeenth aspects, in which removing the excess solution from the multifunctional catalyst precursor comprises filtering or decanting the excess solution from the multifunctional catalyst precursor and drying the multifunctional catalyst precursor to remove solvent.

A nineteenth aspect of the present disclosure may include any of the first through eighteenth aspects, in which the first metal catalyst comprises molybdenum and the second metal catalyst comprises cobalt, where at least the heteropolyacid includes the molybdenum.

A twentieth aspect of the present disclosure may be directed to the multifunctional catalyst produced by the methods and processes of any of the first through nineteenth aspects.

A twenty-first aspect of the present disclosure may be directed to a multifunctional catalyst for upgrading pyrolysis oil, the multifunctional catalyst comprising one or more cobalt compounds, one or more molybdenum compounds, and phosphorous supported on a hierarchical mesoporous zeolite support. At least one of the molybdenum compounds, cobalt compounds, or phosphorous may be provided by a heteropolyacid precursor, and the hierarchical mesoporous zeolite support may have an average pore size of from 2 nanometers to 40 nanometers as determined by BJH analysis.

A twenty-second aspect of the present disclosure may include any of the first thorugh twenty-first aspects, in which the first metal catalyst is the heteropolyacid and comprises molybdenum and the second metal catalyst comprises cobalt.

A twenty-third aspect of the present disclosure may include any of the first through twenty-second aspects, in which the multifunctional catalyst comprises phosphorous deposited on the outer surfaces and pore surfaces of the hierarchical mesoporous zeolite support.

A twenty-fourth aspect of the present disclosure may include any of the first through twenty-third aspects, where the multifunctional catalyst has an acidity of less than 15,000 micromoles of ammonia per gram ($\mu mol(NH_3)/g$).

A twenty-fifth aspect of the present disclosure may include any of the first through twenty-fourth aspects, in which the multifunctional catalyst has an acidity of from 1,000 $\mu mol(NH_3)/g$ to 15,000 $\mu mol(NH_3)/g$.

A twenty-sixth aspect of the present disclosure may include any of the first through twenty-fifth aspects, in which the multifunctional catalyst has a BET surface area of from 300 meters squared per gram to 700 meters squared per gram.

A twenty-seventh aspect of the present disclosure may include any of the first through twenty-sixth aspects, in which a method for upgrading pyrolysis oil may include contacting the pyrolysis oil with the multifunctional catalyst of any of the first through twenty-sixth aspects at mild reaction conditions comprising reaction temperatures of less than 500 degrees Celsius and pressures less than 6 megapascals. The pyrolysis oil may include multi-ring aromatic compounds. Contacting the pyrolysis oil with the multifunctional catalyst at the reaction conditions may convert at least a portion of the multi-ring aromatic compounds in the pyrolysis oil to one or more C6-C8 aromatic compounds.

In a twenty-eighth aspect of the present disclosure, a method for upgrading pyrolysis oil may include contacting the pyrolysis oil with a multifunctional catalyst at mild reaction conditions comprising reaction temperatures of less than 500 degrees Celsius (° C.) and pressures less than 6 megapascals (MPa). The pyrolysis oil may include multi-ring aromatic compounds. The multifunctional catalyst may be produced by a process comprising contacting a hierarchical mesoporous zeolite support with a solution comprising at least a first metal catalyst precursor and a second metal catalyst precursor. The hierarchical mesoporous zeolite support may have an average pore size of from 2 nanometers to 40 nanometers as determined by Barrett-Joyner-Halenda (BJH) analysis, the first metal catalyst precursor, the second metal catalyst precursor, or both, may include a heteropolyacid, and the contacting deposits the first metal catalyst precursor and the second catalyst precursor onto outer surfaces and pore surfaces of the hierarchical mesoporous zeolite support to produce a multifunctional catalyst precursor. The process for producing the multifunctional catalyst may further include removing excess solution from the multifunctional catalyst precursor and calcining the multifunctional catalyst precursor to produce the multifunctional catalyst. The multifunctional catalyst comprises at least a first metal catalyst and a second metal catalyst supported on the zeolite support. Contact of the pyrolysis oil with the multifunctional catalyst at the reaction conditions may convert at least a portion of the multi-ring aromatic compounds in the pyrolysis oil to one or more C6-C8 aromatic compounds.

A twenty-ninth aspect of the present disclosure may include either the twenty-seventh or twenty-eighth aspects, in which the C6-C8 aromatic compounds include one or more of benzene, toluene, ethylbenzene, xylene, or combinations of these.

A thirtieth aspect of the present disclosure may include any of the twenty-seventh through twenty-ninth aspects, in which contacting the pyrolysis oil with the multifunctional catalyst at the reaction conditions may convert the portion of the multi-ring aromatic compounds in the pyrolysis oil to C6-C8 aromatic compounds in a single step, without conducting a subsequent chemical reaction step.

A thirty-first aspect of the present disclosure may include any of the twenty-seventh through thirtieth aspects, where contacting the pyrolysis oil with the multifunctional catalyst may result a yield of C6-C8 aromatic compounds of at least 30 percent (%).

A thirty-second aspect of the present disclosure may include any of the twenty-seventh through thirty-first aspects, further comprising separating an upgraded pyrolysis oil from the multifunctional catalyst.

A thirty-third aspect of the present disclosure may include any of the twenty-seventh through thirty-second aspects, in which the pyrolysis oil is contacted with the multifunctional catalyst at a temperature of from 380 degrees Celsius to 400 degrees Celsius.

A thirty-fourth aspect of the present disclosure may include any of the twenty-seventh through thirty-third aspects, in which the pyrolysis oil may be contacted with the multifunctional catalyst at a pressure less than or equal to 5 megapascals.

A thirty-fifth aspect of the present disclosure may include any of the twenty-seventh through thirty-fourth aspects, in which the pyrolysis oil is contacted with the multifunctional catalyst at a pressure of from 0.1 megapascal to 5 megapascals.

It should now be understood that various aspects of the multifunctional catalyst for upgrading pyrolysis oil, methods of making the multifunctional catalyst for upgrading pyrolysis oil using heteropolyacids as the metal catalyst precursors, and methods of upgrading pyrolysis oils using the methods are described and such aspects may be utilized in conjunction with various other aspects.

Throughout this disclosure, ranges are provided for various properties and characteristics of the multifunctional catalyst and various processing parameters and operating conditions for the methods for making the multifunctional catalyst and upgrading pyrolysis oil. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges, which may be formed within the provided bounds, such as 1-8, 2-4, 6-9, and 1.3-5.6.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

What is claimed is:

1. A method of making a multifunctional catalyst for upgrading pyrolysis oil, the method comprising:
    contacting a hierarchical mesoporous zeolite support with a solution comprising at least a first metal catalyst precursor and a second metal catalyst precursor, where:
        the hierarchical mesoporous zeolite support has an average pore size of from 2 nanometers to 40 nanometers as determined by Barrett-Joyner-Halenda (BJH) analysis;
        the first metal catalyst precursor, the second metal catalyst precursor, or both, comprises a heteropolyacid having at least one heteroatom selected from the group consisting of phosphorous, silicon, germanium, arsenic, and combinations of these; and
        the contacting deposits the first metal catalyst precursor and the second metal catalyst precursor onto outer surfaces and pore surfaces of the hierarchical mesoporous zeolite support to produce a multifunctional catalyst precursor;
    removing excess solution from the multifunctional catalyst precursor; and
    calcining the multifunctional catalyst precursor to produce the multifunctional catalyst comprising at least a first metal catalyst and a second metal catalyst deposited on the outer surfaces and pore surfaces of the hierarchical mesoporous zeolite support.

2. The method of claim 1, in which the hierarchical mesoporous zeolite support comprises a hierarchical mesoporous beta zeolite support.

3. The method of claim 1, in which the hierarchical mesoporous zeolite support has an average pore size of from 5 nanometers to 25 nanometers as determined by BJH analysis.

4. The method of claim 1, in which the hierarchical mesoporous zeolite support has a total pore volume of greater than or equal to 0.35 cubic centimeters per gram.

5. The method of claim 1, in which the hierarchical mesoporous zeolite support comprises a molar ratio of silica to alumina of from 20 to 100.

6. The method of claim 1, further comprising producing the hierarchical mesoporous zeolite support.

7. The method of claim 6, in which producing the hierarchical mesoporous zeolite support comprises converting a microporous parent zeolite into the hierarchical mesoporous zeolite support through desilication of the microporous parent zeolite.

8. The method of claim 7, in which desilication of the microporous parent zeolite to produce the hierarchical mesoporous zeolite support comprises:
    mixing the microporous zeolite with an aqueous metal hydroxide solution; and
    heating the microporous zeolite and aqueous metal hydroxide mixture to a temperature of greater than or equal to 100 degrees Celsius to produce the hierarchical mesoporous zeolite support.

9. The method of claim 1, in which the heteropolyacid comprises:
    at least one metal selected from cobalt, molybdenum, vanadium, or combinations of these.

10. The method of claim 1, in which the first metal catalyst precursor comprises the heteropolyacid.

11. The method of claim 1, in which the first metal catalyst precursor comprises a first heteropolyacid and the second metal catalyst precursor comprises a second heteropolyacid that is different from the first heteropolyacid.

12. The method of claim 11, in which the first heteropolyacid or the second heteropolyacid is $H_3PMo_{12}O_{40}$.

13. The method of claim 1, in which the heteropolyacid comprises phosphormolybdic hetereopolyacid having formula $H_3PMo_{12}O_{40}$.

14. The method of claim 1, in which removing the excess solution from the multifunctional catalyst precursor comprises filtering or decanting the excess solution from the multifunctional catalyst precursor and drying the multifunctional catalyst precursor to remove solvent.

15. The method of claim 1, in which the first metal catalyst comprises molybdenum and the second metal catalyst comprises cobalt, where at least the heteropolyacid includes the molybdenum.

16. The method of claim 1, in which the multifunctional catalyst comprises phosphorous deposited on the outer surfaces and pore surfaces of the hierarchical mesoporous zeolite support.

17. The method of claim 1, in which the hierarchical mesoporous zeolite support comprises an acidity of less than 15,000 micromoles of ammonia per gram.

* * * * *

UNITED STATES PATENT AND TRADEMARK OFFICE
CERTIFICATE OF CORRECTION

Page 1 of 1

PATENT NO. : 10,953,396 B2
APPLICATION NO. : 16/502601
DATED : March 23, 2021
INVENTOR(S) : Miao Sun, Ke Zhang and Veera Venkata R Tammana It is certified that error appears in the above-identified patent and that said Letters Patent is hereby corrected as shown below:

On the Title Page

Item (73), assignee 2, delete "Aramco Services Company (Houston, TX)"

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*